United States Patent
Tawil et al.

(10) Patent No.: US 11,693,140 B2
(45) Date of Patent: Jul. 4, 2023

(54) IDENTIFYING HYDROCARBON RESERVES OF A SUBTERRANEAN REGION USING A RESERVOIR EARTH MODEL THAT MODELS CHARACTERISTICS OF THE REGION

(71) Applicant: Saudi Arabian Oil Company, Dhahran (SA)

(72) Inventors: Aus A. Tawil, Dhahran (SA); Matter J. Alshammery, Dhahran (SA); Nazih F. Najjar, Dhahran (SA); Mohammad O. Amoudi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 213 days.

(21) Appl. No.: 16/844,959

(22) Filed: Apr. 9, 2020

(65) Prior Publication Data

US 2021/0319304 A1 Oct. 14, 2021

(51) Int. Cl.
| | |
|---|---|
| *G01V 1/28* | (2006.01) |
| *G06F 30/27* | (2020.01) |
| *E21B 49/00* | (2006.01) |
| *G01V 1/30* | (2006.01) |
| *G06N 3/04* | (2023.01) |

(Continued)

(52) U.S. Cl.
CPC .............. *G01V 1/282* (2013.01); *E21B 49/00* (2013.01); *G01V 1/301* (2013.01); *G01V 1/48* (2013.01); *G06F 30/27* (2020.01); *G06N 3/04* (2013.01); *E21B 2200/20* (2020.05); *G01N 33/241* (2013.01); *G01V 1/306* (2013.01);
*G01V 99/005* (2013.01); *G01V 2210/643* (2013.01); *G06F 2111/10* (2020.01); *G06N 3/08* (2013.01)

(58) Field of Classification Search
USPC .............................................. 706/12; 702/11
See application file for complete search history.

(56) References Cited

U.S. PATENT DOCUMENTS

| | | | |
|---|---|---|---|
| 7,248,259 | B2 | 7/2007 | Fremming |
| 7,546,228 | B2 | 6/2009 | Cullick et al. |

(Continued)

FOREIGN PATENT DOCUMENTS

| | | |
|---|---|---|
| AU | 2012203388 | 1/2013 |
| EP | 0674189 | 12/2000 |

(Continued)

OTHER PUBLICATIONS

Aldawood et al., "Integrated Pre-Well Planning Process Improves Service Quality and Decreases Risk through Cooperation between Drilling and Geosciences." SPE Middle East Oil and Gas Show and Conference. OnePetro, Sep. 2011, 8 pages.

(Continued)

*Primary Examiner* — Paul D Lee
(74) *Attorney, Agent, or Firm* — Fish & Richardson P.C.

(57) ABSTRACT

Methods and systems, including computer programs encoded on a computer storage medium can be used for an integrated methodology that can be used by a computing system to automate processes for generating, and updating (e.g., in real-time), subsurface reservoir models. The methodology and automated approaches employ technologies relating to machine learning and artificial intelligence (AI) to process seismic data and information relating to seismic facies.

20 Claims, 17 Drawing Sheets

(51) Int. Cl.
*G01V 1/48* (2006.01)
*G06F 111/10* (2020.01)
*G06N 3/08* (2023.01)
*G01V 99/00* (2009.01)
*G01N 33/24* (2006.01)

(56) References Cited

U.S. PATENT DOCUMENTS

| | | | |
|---|---|---|---|
| 7,565,243 | B2 | 7/2009 | Kim et al. |
| 7,596,176 | B2 | 9/2009 | Eleftheriou et al. |
| 7,660,711 | B2 | 2/2010 | Pita et al. |
| RE41,999 | E | 12/2010 | Thomas et al. |
| 8,612,195 | B2 | 12/2013 | Sun et al. |
| 8,670,966 | B2 | 3/2014 | Rashid et al. |
| 8,793,111 | B2 | 7/2014 | Tilke et al. |
| 8,849,640 | B2 | 9/2014 | Holl et al. |
| 9,175,557 | B2 | 11/2015 | Iversen et al. |
| 9,187,984 | B2 | 11/2015 | Usadi et al. |
| 9,581,723 | B2 | 2/2017 | Hurley et al. |
| 9,645,575 | B2 | 5/2017 | Watson |
| 9,747,393 | B2 | 8/2017 | Dasari |
| 10,068,186 | B2 | 9/2018 | Shi et al. |
| 10,088,984 | B2 | 10/2018 | Plummer et al. |
| 10,127,477 | B2 | 11/2018 | Chen et al. |
| 10,141,073 | B2 | 11/2018 | Chin et al. |
| 10,148,677 | B2 | 12/2018 | Muddu et al. |
| 10,157,217 | B2 | 12/2018 | Gomes et al. |
| 10,157,343 | B1 | 12/2018 | Lin et al. |
| 10,157,479 | B2 | 12/2018 | Estrada et al. |
| 10,163,234 | B1 | 12/2018 | Kim et al. |
| 10,167,713 | B2 | 1/2019 | Ma et al. |
| 10,192,051 | B2 | 1/2019 | Dell'anno et al. |
| 10,209,974 | B1 | 2/2019 | Patton et al. |
| 10,223,482 | B2 | 3/2019 | Borrel et al. |
| 10,364,662 | B1 | 7/2019 | Basu et al. |
| 2004/0122640 | A1 | 6/2004 | Dusterhoft |
| 2004/0225441 | A1 | 11/2004 | Tilke et al. |
| 2005/0043548 | A1 | 2/2005 | Cates |
| 2007/0156341 | A1 | 7/2007 | Langlais et al. |
| 2010/0332139 | A1 | 12/2010 | Bruun |
| 2011/0063292 | A1 | 3/2011 | Holl et al. |
| 2011/0257766 | A1 | 10/2011 | Sundaram et al. |
| 2012/0232859 | A1 | 9/2012 | Pomerantz et al. |
| 2012/0281500 | A1 | 11/2012 | Hoekstra |
| 2012/0325556 | A1 | 12/2012 | Luxey |
| 2015/0185715 | A1 | 7/2015 | McHugh |
| 2017/0067325 | A1* | 3/2017 | Garcia Zurita ......... E21B 43/00 |
| 2017/0116436 | A1 | 4/2017 | Wu et al. |
| 2017/0205531 | A1 | 7/2017 | Berard et al. |
| 2017/0242410 | A1 | 8/2017 | Iyer et al. |
| 2017/0335665 | A1 | 11/2017 | Saleri et al. |
| 2017/0337302 | A1 | 11/2017 | Mezghani et al. |
| 2018/0031721 | A1 | 2/2018 | Etiene Queiroz et al. |
| 2018/0230780 | A1 | 8/2018 | Klenner et al. |
| 2019/0025461 | A1 | 1/2019 | Wiener et al. |
| 2019/0093469 | A1 | 3/2019 | Williams et al. |
| 2019/0094403 | A1 | 3/2019 | Prochnow et al. |
| 2019/0094414 | A1 | 3/2019 | Prochnow et al. |
| 2019/0095792 | A1 | 3/2019 | Kashinath |
| 2019/0107642 | A1 | 4/2019 | Farhadi Nia et al. |
| 2019/0107643 | A1 | 4/2019 | Golmohammadizangabad et al. |
| 2019/0107644 | A1 | 4/2019 | Farhadi Nia |
| 2019/0107645 | A1 | 4/2019 | Nolan et al. |
| 2019/0179983 | A1 | 6/2019 | Prochnow et al. |
| 2019/0197208 | A1 | 6/2019 | Borrel et al. |
| 2019/0227191 | A1 | 7/2019 | Raman et al. |
| 2019/0244129 | A1* | 8/2019 | Tabuchi ................. G06N 20/20 |
| 2019/0333164 | A1 | 10/2019 | Fox et al. |
| 2020/0019882 | A1 | 1/2020 | Garg et al. |
| 2020/0183047 | A1* | 6/2020 | Denli ...................... G06F 17/18 |
| 2021/0317726 | A1 | 10/2021 | Tawil et al. |
| 2021/0318464 | A1 | 10/2021 | Tawil et al. |

FOREIGN PATENT DOCUMENTS

| | | |
|---|---|---|
| EP | 1679424 | 7/2006 |
| EP | 1728967 | 12/2006 |
| EP | 2198121 | 6/2010 |
| GB | 2325523 | 11/1998 |
| WO | WO 2004069960 | 8/2004 |
| WO | WO 2010014128 | 2/2010 |
| WO | WO 2012027020 | 3/2012 |
| WO | WO 2012096663 | 7/2012 |
| WO | WO 2017116436 | 7/2017 |
| WO | WO 2018217875 | 11/2018 |
| WO | WO 2019055565 | 3/2019 |
| WO | WO 2019241062 | 12/2019 |

OTHER PUBLICATIONS

PCT International Search Report and Written Opinion in International Appln. No. PCT/US2021/026401, dated Jul. 7, 2021, 12 pages.

PCT International Search Report and Written Opinion in International Appln. No. PCT/US2021/026619, dated Jul. 9, 2021, 13 pages.

An et al, "A Grid-based Index Method for Time Warping Distance," Lecture Notes in Computer Science, vol. 3129, pp. 65-75, 2004, 11 pages.

Brulé, "The Data Reservoir: How Big Data Technologies Advance Data Management and Analytics in E&P," SPE-173445-MS, SPE Digital Energy Conference and Exhibition, The Woodlands, Texas, USA, Mar. 2016, 7 pages.

Hof et al, "Recent developments in model-based optimization and control of subsurface flow in oil reservoirs," Dynamic Networks: Data-Driven Modeling and Control, Proceedings of the 2012 IFAC Workshop on Automatic Control in Offshore Oil and Gas Production, May 31-Jun. 1, 2012, Trondheim, Norway, 12 pages.

Lecourtier, "Interactive Drilling for Fast Track Oilfield Development," Proceedings of the seminar held in Rueil-Malmaison, Nov. 1999; ISBN 2-7-108-0804-8, IFP, Techmp, Paris, 2001.

Mueen et al, "Extracting Optimal Performance from Dynamic Time Warping," Proceedings of the 22nd ACM SIGKDD International Conference on Knowledge Discovery and Data Mining, San Francisco, California, Aug. 2016, pp. 2129-2130, 2 pages.

Popa et al, "Intelligent Use of Big Data for Heavy Oil Reservoir Management," SPE-174912-MS, SPE Annual Technical Conference and Exhibition, Houston, Texas, USA, Sep. 2015, 14 pages.

Saikia, "Real-Time Modeling-While-Drilling for Optimized Geosteering and Enhanced Horizontal Well Placement in Thin and Complex Reservoirs," IPTC-16715-MS, International Petroleum Technology Conference, Mar. 26-28, 2013, Beijing, China, 8 pages.

Schroeder et al, "Real-Time Geological Positioning of a Well in the North Sea," SPE-71744-MS, SPE Annual Technical Conference and Exhibition, Sep.-Oct. 2001, New Orleans, Louisiana, 7 pages.

Thevoux-Chabuel, "Integrating real-time drilling information into the geological model," First Break, Jul. 2009, 7: 63-67.

PCT International Search Report and Written Opinion in International Appln. No. PCT/US2021/026334, dated Jul. 21, 2021, 17 pages.

Diez et al., "Opportunities and challenges of using sequential quadratic programming (SQP) for optimization of petroleum production network" European Symposium on Computer Aided Process Engineering, Jan. 2005, 169-174, 6 pages.

* cited by examiner

| MODULE | CURRENT SYSTEM SPEED (DAYS) | PREDICTED iLEM SYSTEM SPEED (DAYS) | ESTIMATED TIME SAVE % |
|---|---|---|---|
| BP&R | 30 | 7 | 77% |
| WDS | 1 | 0.5 | 50% |
| GDS | 7 | 2 | 71% |
| E-HoW | 10 | 3 | 70% |
| FTAP | 3 | 0.5 | 83% |
| GMP | 100 | 20 | 80% |
| RCAT | 30 | 1 | 97% |
| 3DEMDS | 7 | 2 | 71% |
| 3DMU | 30 | 5 | 83% |
| SWG | 14 | 7 | 50% |
| WPO | 3 | 0.5 | 83% |
| WAS | 3 | 0.5 | 83% |
| RPV&EO | 5 | 1 | 80% |
| TOTAL | 243 | 50 | 79% |

Fig. 15

IDENTIFYING HYDROCARBON RESERVES OF A SUBTERRANEAN REGION USING A RESERVOIR EARTH MODEL THAT MODELS CHARACTERISTICS OF THE REGION

TECHNICAL FIELD

This specification relates to identifying characteristics of a subterranean region.

BACKGROUND

In geology, sedimentary facies are bodies of sediment that are recognizably distinct from adjacent sediments that resulted from different depositional environments. Generally, geologists distinguish facies by aspects of the rock or sediment being studied. Seismic facies are groups of seismic reflections whose parameters (such as amplitude, continuity, reflection geometry, and frequency) differ from those of adjacent groups. Seismic facies analysis is a subdivision of seismic stratigraphy and plays an important role in hydrocarbon exploration and is one key step in the interpretation of seismic data for reservoir characterization. The seismic facies in a given geological area can provide useful information, particularly about the types of sedimentary deposits and the anticipated lithology.

In reflection seismology, geologists and geophysicists perform seismic surveys to map and interpret sedimentary facies and other geologic features for applications such as identification of potential petroleum reservoirs. Seismic surveys are conducted by using a controlled seismic source (for example, a seismic vibrator or dynamite) to create a seismic wave. In land-based seismic surveys, the seismic source is typically located at ground surface. The seismic wave travels into the ground, is reflected by subsurface formations, and returns to the surface where it is recorded by sensors called geophones. Other approaches to gathering data about the subsurface (e.g., well logging) can be used to complement the seismic data Reservoir models based on data about the subterranean regions can be used to perform processes relating to field operations.

SUMMARY

Techniques are described for an integrated methodology that can be used by a computing system to automate processes for generating, and updating (e.g., in real-time), subsurface reservoir models. The methodology and automated approaches employ technologies relating to machine learning and artificial intelligence (AI) to process seismic data and information relating to seismic facies. The reservoir models can be used to perform processes relating to hydrocarbon exploration, well planning, geo-steering, reservoir modeling, field development plan generation, and resource allocation for well planning operations. The outputs generated from these processes, including the data processing techniques of the applications, can be enhanced or optimized in response to the continuous adapting and updating of the analytical rules of the integrated multi-dimensional model.

For example, the techniques can be implemented using predictive and autonomous software controls that are derived initially from trained neural networks of a machine-learning (ML) engine. More specifically, the machine-learning engine can generate multiple predictive models in response to processing various types of information and datasets of seismic data using one or more neural networks. The predictive models cooperate to form an integrated multi-dimensional geological model, such as a subsurface reservoir model.

In some implementations, the integrated multi-dimensional geological model is a reservoir earth model that employs different analytical rules. Each of the analytical rules are continuously adapted and improved based on the AI and ML technologies of the ML engine. The multi-dimensional geological model also includes multiple application programs, where each of the application programs can employ a subset of the different analytical rules of the geological model.

The application programs are executed at the computing system to perform processes relating to hydrocarbon exploration, well planning, geo-steering, reservoir modeling, field development plan generation, and resource allocation for well planning operations. The outputs generated from these processes, including the data processing techniques of the applications, can be enhanced or optimized in response to the continuous adapting and updating of the analytical rules of the integrated multi-dimensional model.

One aspect of the subject matter described in this specification can be embodied in a computer-implemented method for determining characteristics of an underground formation in a subterranean region of a geological area. The method includes obtaining a first wavefield represented by seismic data generated from multiple sampling sensors, wherein a subset of the sampling sensors are deployed in the subterranean region; and providing data values of the seismic data that indicate properties of the underground formation as inputs to a machine-learning engine configured to generate one or more models.

The method includes processing the inputs corresponding to data values of the seismic data using the machine-learning engine; in response to processing the data values of the seismic data, generating multiple predictive models, each predictive model being configured to determine geological properties of a layer in the underground formation based on a respective analytical rule of the predictive model; and providing, to each of the predictive models, new data values of seismic data representing a second wavefield obtained using the subset of sampling sensors. The method includes automatically updating the respective analytical rule of each predictive model in response to processing the new data values of seismic data at the predictive model; and determining, from the new data values of seismic data, (i) a first geological property of the layer using the updated analytical rule of a first predictive model and (ii) a second, different geological property of the layer using the updated analytical rule of a second, different predictive model.

These and other implementations can each optionally include one or more of the following features. For example, in some implementations, the method includes: generating an integrated multi-dimensional geological model based on the plurality of predictive models, wherein the integrated multi-dimensional geological model is configured to model characteristics of reservoirs in the subterranean region to estimate hydrocarbon reserves using at least the first and second geological properties of the layer in the underground formation.

Obtaining each of the first and second wavefields includes obtaining each of the first and second wavefields in response to drilling the subterranean region to penetrate one or more layers in the underground formation. The method includes determining, by the integrated multi-dimensional geological model, a position of one or more well bores in the subterranean region based on the modeled characteristics of reservoirs in the subterranean region and estimates of hydrocarbon reserves in the reservoirs.

The method includes determining respective quality measures of sediments in each of the one or more layers using each predictive model of the multiple predictive models; and based on the respective quality measure of sediments in each of the one or more layers, determining, by the integrated multi-dimensional geological model, a trajectory for drilling the subterranean region to penetrate the one or more layers in the underground formation. In some implementations, generating the plurality of predictive models comprises: generating a three-dimensional geological numerical model configured to predict numerical values indicating one or more properties of the layer in the underground formation. In some implementations, generating the plurality of predictive models comprises generating a plurality of permanently active autonomous predictive models.

In some implementations, processing the inputs corresponding to the data values of the seismic data includes: processing the inputs using one or more neural networks of the machine-learning engine based on analytical rules executed at the machine-learning engine, wherein each of the one or more neural network is configured to represent a respective data model of the machine-learning engine. At least one of the analytical rules can be a deep-learning algorithm that is executed to process the inputs through one or more layers of a neural network; and the neural network is implemented on a hardware circuit accessible by the machine-learning engine.

Other implementations of this and other aspects include corresponding systems, apparatus, and computer programs, configured to perform the actions of the methods, encoded on computer storage devices. A computing system of one or more computers or hardware circuits can be so configured by virtue of software, firmware, hardware, or a combination of them installed on the system that in operation cause the system to perform the actions. One or more computer programs can be so configured by virtue of having instructions that are executable by a data processing apparatus to cause the apparatus to perform the actions.

The subject matter described in this specification can be implemented to realize one or more of the following advantages. The described techniques provide an improved computing system that employs an innovative methodology for generating an integrated multi-dimensional geological model corresponding to a reservoir earth model. The earth model is based on the integration of multiple predictive models that are generated at a ML engine of an example AI data processing system. Each of the predictive models employs adaptive analytics that are based on the iterative processing of new seismic data at a prior trained neural network model (e.g., a predictive model).

The iterative processing with respect to each predictive model allows the model to continuously refine its analytical rules to improve the overall data processing capabilities of the reservoir earth model. The data processing capabilities of the earth model allow for computing more accurate estimations of hydrocarbon reserves in underground formations as well as improved precision, placement, and control of machinery during well drilling operations. In some cases, the improved computing system employs autonomous communications methods and automated workflows that enable geoscientists to accelerate subsurface characterization and field development processes for locating hydrocarbon reserves in a reservoir of an underground formation.

The details of one or more embodiments of these systems and methods are set forth in the accompanying drawings and the description to be presented. Other features, objects, and advantages of these systems and methods will be apparent from the description and drawings, and from the claims.

BRIEF DESCRIPTION OF THE DRAWINGS

FIG. 15 illustrates a table that shows examples of estimated time savings for modules of an example reservoir earth model.

Like reference numbers and designations in the various drawings indicate like elements.

DETAILED DESCRIPTION

This specification describes systems and techniques for generating a multi-dimensional geological model that optimizes outcomes of hydrocarbon exploration relative to prior systems. For example, the multi-dimensional geological model can be a reservoir Earth Model (REM) that is configured to improve and accelerate subsurface characterization, including field development processes for hydrocarbon exploration and related well planning and geo-steering operations. Example implementations relating to these concepts are described in more detail later at least with reference to FIGS. 1-5.

This specification also describes systems and techniques for performing probabilistic modeling of reservoir properties in a subterranean region using well logs and relevant seismic data. The probabilistic modeling can include generating risks map that indicate uncertainties about characteristics and properties of areas in an underground formation. The probabilistic models and risk maps are used to compute estimates of hydrocarbon reserves at the particular area of a reservoir in the region. Example implementations relating to these concepts are described in more detail later at least with reference to FIGS. 6-12.

This specification also describes improved techniques for generating field development plans and allocating resources for drilling activity to enhance business performance and commercial viability of well-planning operations. The adaptive analytics of the integrated multi-dimensional geological model are used to determine resource requirements, including identifying geological project-level requirements for the operations. Resources defined by the requirements are used to execute tasks of a field development plan that correspond to drilling activity for extracting hydrocarbons of a reservoir within cost constraints of a corporate business plan. Example implementations relating to these concepts are described in more detail later at least with reference to FIGS. 13-16.

Figure 1:
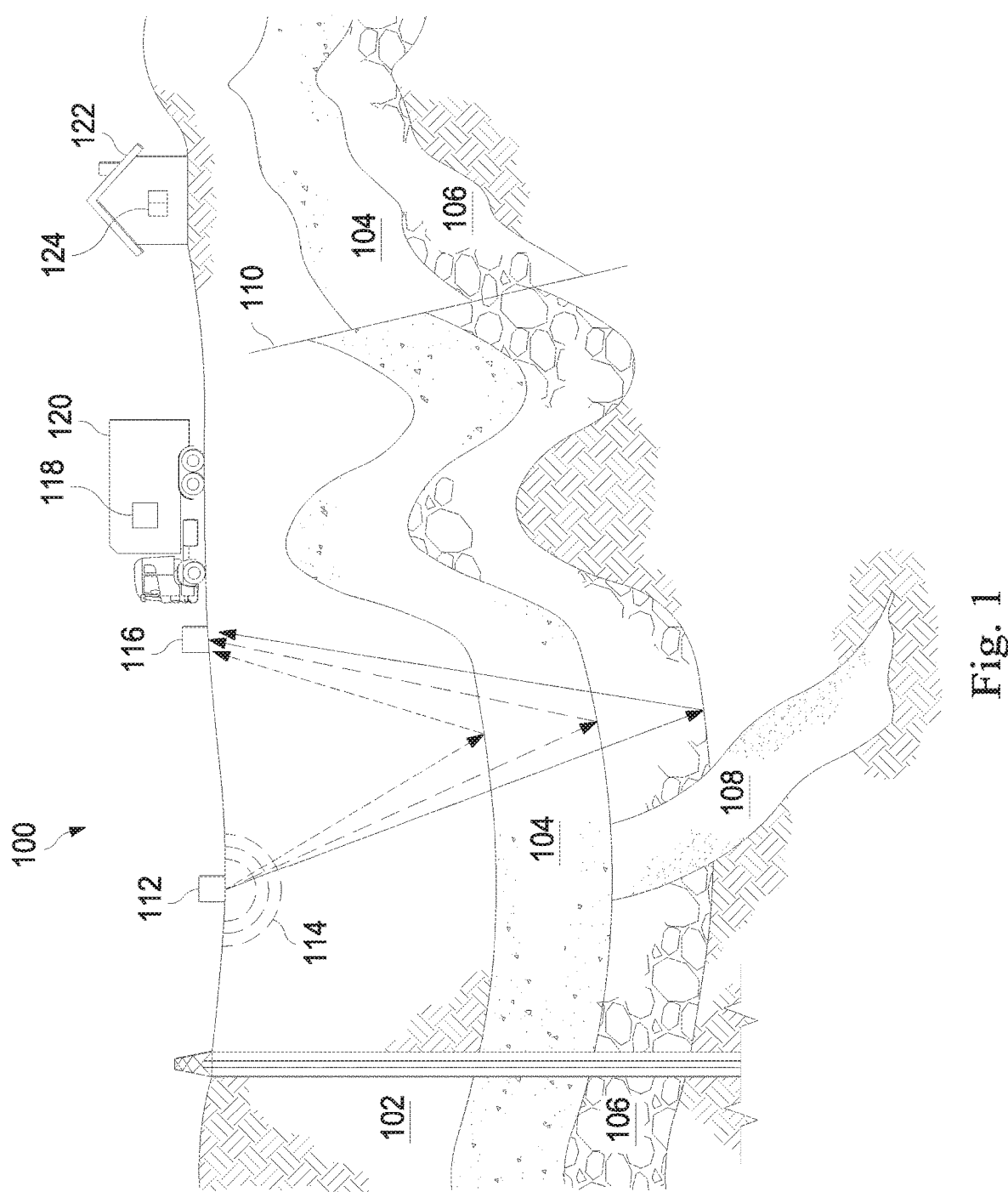
FIG. 1 is a schematic view of a seismic survey being performed to map subterranean features such as facies and faults.

FIG. 1 is a schematic view of a seismic survey being performed to map subterranean features such as facies and faults in a subterranean formation 100. The subterranean formation 100 includes a layer of impermeable cap rocks 102 at the surface. Facies underlying the impermeable cap rocks 102 include a sandstone layer 104, a limestone layer 106, and a sand layer 108. A fault line 110 extends across the sandstone layer 104 and the limestone layer 106.

Subterranean features can be mapped using seismic data that represents elastic multi-component wavefields. In performing seismic surveys, elastic waves are generated by the seismic survey equipment whose reflections/refractions are received by sensor devices or geophones. Such elastic waves can include primary waves (P-waves) and secondary waves (S-waves). P-waves are compressional waves that are longitudinal in nature, whereas S-waves are shear waves that are transversal in nature. In some cases, P- and S-wave components of a wavefield can be extracted and processed separately as either pure P-wave mode data or pure S-wave mode data.

A seismic source 112 (for example, a seismic vibrator or an explosion) generates seismic waves 114 that propagate in the earth. The velocity of these seismic waves depends on properties that include density, porosity, and fluid content of the medium through which the seismic waves are traveling. Different geologic bodies or layers in the earth are distinguishable because the layers have different properties and, thus, different characteristic seismic velocities. For example, in the subterranean formation 100, the velocity of seismic waves traveling through the subterranean formation 100 will be different in the sandstone layer 104, the limestone layer 106, and the sand layer 108. As the seismic waves 114 contact interfaces between geologic bodies or layers that have different velocities, the interface reflects some of the energy of the seismic wave and refracts part of the energy of the seismic wave. Such interfaces are sometimes referred to as horizons.

The seismic waves 114 are received by a sensor or sensors 116. Although illustrated as a single component in FIG. 1, the sensor or sensors 116 are typically a line or an array of sensors 116 that generate an output signal in response to received seismic waves including waves reflected by the horizons in the subterranean formation 100. The sensors 116 can be geophone-receivers that produce electrical output signals transmitted as input data, for example, to a computer 118 on a seismic control truck 120. Based on the input data, the computer 118 may generate a seismic data output, such as a seismic two-way response time plot.

A control center 122 can be operatively coupled to the seismic control truck 120 and other data acquisition and wellsite systems. The control center 122 may have computer facilities for receiving, storing, processing, and analyzing data from the seismic control truck 120 and other data acquisition and wellsite systems. For example, computer systems 124 in the control center 122 can be configured to analyze, model, control, optimize, or perform management tasks of field operations associated with development and production of resources such as oil and gas from the subterranean formation 100. Alternatively, the computer systems 124 can be located in a different location other than the control center 122. Some computer systems are provided with functionality for manipulating and analyzing the data, such as performing seismic interpretation or borehole resistivity image log interpretation, to identify geological surfaces in the subterranean formation or performing simulation, planning, and optimization of production operations of the wellsite systems.

In some embodiments, results generated by the computer system 124 may be displayed for user viewing using local or remote monitors or other display units. One approach to analyzing seismic data is to associate the data with portions of a seismic cube representing represent the subterranean formation 100. The seismic cube can also display results of the analysis of the seismic data associated with the seismic survey.

Figure 2:
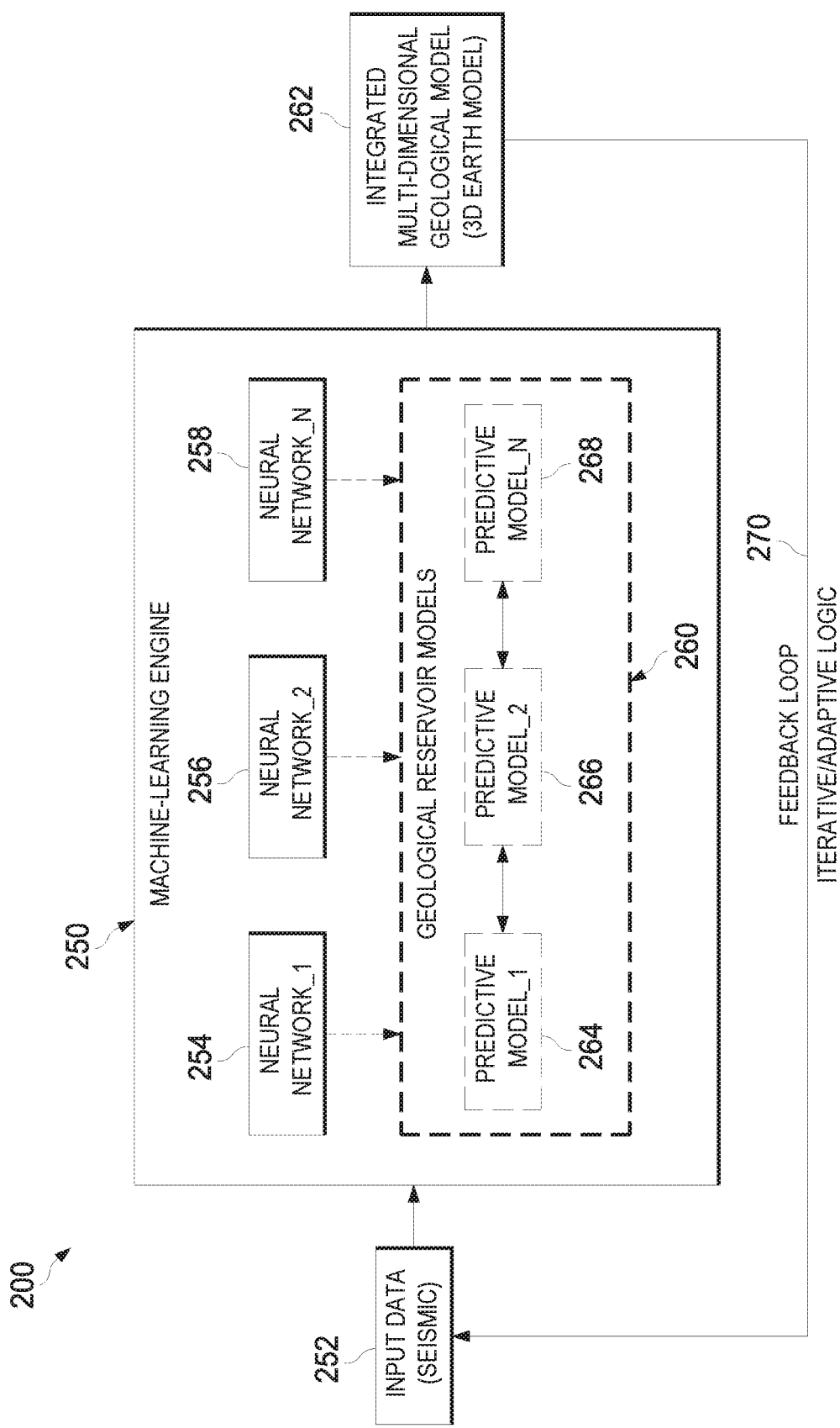
FIG. 2 illustrates an example computing system used to generate predictive models for modeling characteristics of a subterranean region.

FIG. 2 illustrates an example computing device 200 used to generate predictive models for modeling characteristics of a subterranean region. Computing device 200 may be included in the computer system 124 described earlier with reference to FIG. 1. For example, the computing device 200 can be included in the computer system 124 as a sub-system of hardware circuits, such as a special-purpose circuit, that includes one or more processor microchips. In general, computing device 200 can include processors, for example, a central processing unit (CPU) and a graphical processing unit (GPU), memory, and data storage devices that collectively form one or more computing devices 200 of computer systems 124.

Referring to FIG. 2, computing device 200 includes a machine-learning engine 250 ("ML engine 250") that is configured to process input data 252 to generate one or more predictive models. For example, the ML engine 250 can receive a set of seismic data 252 and process the received seismic data using various types of data analysis methods and machine-learning technologies to construct predictive models. In some implementations, computing device 200 is an AI data processing system that is operable to generate multiple predictive models in response to processing information or datasets accessible at the system 100. For example, information and datasets may be collected by the computer systems 124 as well as other data acquisition systems and stored in a data storage device of the system 100 for processing at the ML engine 250.

The data processed by the AI system 200 to generate the predictive models may be annotated training data (described later) that includes one or more sets of features. A feature is generally an attribute or property shared by independent units on which analysis or prediction is to be done. For example, the independent units can be groups of image pixels that form parts of items such as images and other documents. The feature can be an attribute of an object, such as a geological body or sediments in an area, depicted in an image or groups of data values that indicate the density or porosity of the geological body.

In some cases, a feature (or attribute) of an object can be a line or edge in an image, as defined by a group of image pixels. In general, any attribute can be a feature so long as the attribute is useful to performing a desired predictive or deterministic function of a model. Hence, for a given problem such as detecting concentrations of hydrocarbons in a reservoir, a feature can be a characteristic in a set of data that might help when solving the problem, particularly when solving the problem involves making some prediction about the set of data. In the example of detecting concentrations of hydrocarbons, some features can include a range of data values for fluid concentrations or fluid content which are known to indicate a presence of hydrocarbon reserves.

A training dataset can be developed based on a feature engineering process of system 100 that uses various data processing methods to generate a set of features. The features or feature sets can be generated using numerical or other data values of a raw dataset. The raw dataset may be based on information and data obtained from sensors, geophones, or various other sources of seismic data, including sources described in this document. In some implementations, feature sets can be generated using different mathematical computations for deriving features, such as computations based on mean or median data imputation.

For example, the feature engineering process can include using an example imputation algorithm to process a raw feature set of data that describes general attributes of geological bodies in an underground formation. In this example, the raw feature set of data may be processed to generate a modified feature set of data values which are more descriptive of properties and characteristics of a reservoir, such as a density and porosity of layers at the reservoir or a fluid content of the reservoir. Each of the raw feature set and modified feature set can include features and representative data values which are used by the AI data processing system to generate one or more trained models.

System 100 can include a training phase and an implementation phase. During the training phase example data models of ML engine 250 are trained to perform particular types of functions relating to hydrocarbon exploration and extraction, such as reservoir characterization, well placement, and fluid flow dynamic reservoir simulation. The data models may be based on different types of machine-learning technologies and trained in response to processing data values of the input data 252 in accordance with algorithms for the technology.

In the example of FIG. 2, the data models are based on neural networks 254, 256, and 258. In some cases, each of the data models may be based on a single neural network or multiple neural networks. Although neural networks are represented in FIG. 2, in some implementations, the data models can be based on, or include, other types of machine-learning technologies, such as a classifier, a neural network, a feature generator, a support vector machine, a Bayesian network, or other related machine-learning technology.

The input data 252 may be a training dataset that includes sets of features that are processed by trainable neural networks 254, 256, 258. Each of the neural networks 254, 256, 258 may be implemented on a respective hardware computing device of the ML engine 250, such as a special-purpose processor, a GPU accelerator, or application specific circuit. In some cases, a single special-purpose processing device is operable to implement each of multiple neural networks 254, 256, 258. The neural networks of the ML engine 250 are configured to identify, infer, or otherwise learn data patterns and entity relationships in the input data 252 based on algorithms that may be specific to the particular types of neural networks that are implemented at the ML engine 250.

In general, neural networks are computing systems with interconnected nodes that work much like neurons in the human brain. Using algorithms, the neural networks can be trained to recognize hidden patterns and correlations in raw data, cluster and classify data elements according to the correlations and patterns, and continuously learn new correlations or relationship and improve upon prior inferences and predictions. As noted earlier, the ML engine 250 may be also configured to leverage adaptive analytics enabled by other ML technologies, including Gradient Boosting Machine (GBM) algorithms and Random Forest algorithms.

During the training phase, the ML engine 250 generates one or more predictive models 264, 266, 268 in response to training the neural networks by processing the seismic data through layers of the neural networks 254, 256, 258. Two or more of the predictive models 264, 266, 268 may be referred to collectively as geological reservoir models 260. In some implementations, the ML engine 250 generates multiple distinct predictive models that are each configured to perform certain predictive, pattern mining, or inference functions relating to different aspects of hydrocarbon exploration in a subterranean region.

For example, the ML engine 250 can generate a predictive model 264 (e.g., model_1) that is configured to automatically identify and select geological formation tops/surfaces in response to processing data values obtained from well logs as well as control processes for geological well drilling. The ML engine 250 can generate another predictive model 266 (e.g., model_2) that is configured to automatically enhance aspects of a geo-steering process, such as providing improved functions for controlling processes during geological well drilling in response to processing data values relating to well plans and reservoir properties.

The system 100 uses ML engine 250 to generate an integrated multi-dimensional geological model 262. For example, the ML engine 250 generates the integrated multi-dimensional geological model 262 based on predictive models 264, 266, 268. As described in more detail later, the integrated multi-dimensional geological model is generally configured to model characteristics of reservoirs in the subterranean region and to estimate hydrocarbon reserves using at least one or more geological properties of layers and bodies of sedimentary in a subterranean region.

Each of the predictive models 264, 266, 268 that are generated by the ML engine 250 can be uniquely configured to provide a particular predictive function related to improving hydrocarbon exploration, well planning activities, geo-steering, and reservoir modelling, including hydrocarbon reserves estimation and development of well placement programs. In some implementations, the AI data processing system can include N number of neural networks 258, the ML engine 250 is operable to use one or more of the N number of neural networks to generate N number of predictive models, where N is an integer greater than or equal to one.

Each of the predictive models 264, 266, 268 is operable to employ adaptive analytics that are based on the iterative processing of new seismic data at a prior trained neural network data model that forms the computational basis for the predictive model. For example, each of the predictive model 264, 266, 268 is configured to optimize its respective set of analytical rules (for example, rules related identification, selection, analysis, and control functions of the model) based on the adaptive aspects of the model's neural networks that are used to iteratively process new types of input data 252.

In some implementations, information and data related to model outputs may be fed back to the ML engine 250 using an example feedback loop 270. The feedback loop 270 is part of an iterative and adaptive logic of the AI data processing system that is used to iteratively optimize the analytical rules of the predictive models. In some cases, the AI processing system is operable to execute the iterative and adaptive logic to optimize various analytical functions of the integrated multi-dimensional geological model 262. For example, the system 100 can iteratively feedback, in real-time, data values that describe new or different properties of sediments at a layer of a region below a formation top that was selected for a well drilling operation. The data values can be processed at the ML engine 250 to update or enhance the analytical rules of the predictive model to improve upon the model's ability to accurately identify formations that can yield desired estimations of hydrocarbons.

Figure 3:
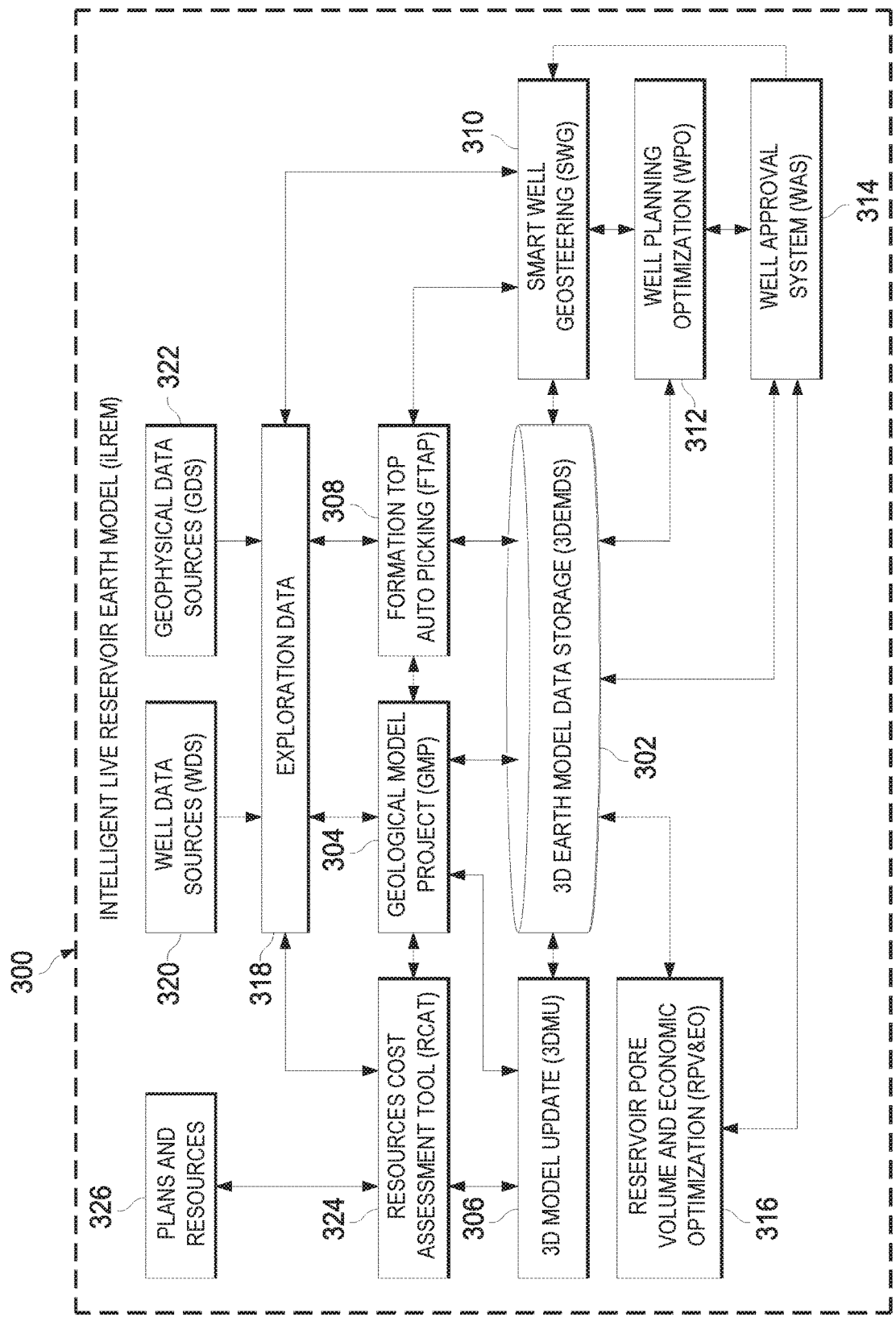
FIG. 3 is a block diagram of an example reservoir earth model.

FIG. 3 is a block diagram of an example reservoir earth model 300 ("earth model 300"). The earth model 300 corresponds to the integrated multi-dimensional geological model 262 described earlier. In some implementations, the earth model 300 is based on at least two of the predictive models generated at the AI data processing device (computing device 200) of FIG. 2. In the example of FIG. 3, the earth model 300 includes multiple component modules. These component modules can correspond to various applications and programs that are available to a user to execute the different geological modelling, predictive computing, and data estimation functions of the earth model 300.

As used in this specification, the term "module" is intended to include, but is not limited to, one or more computers configured to execute one or more software programs that include program code that causes a processing unit(s) of the computer to execute one or more functions. The term "computer" is intended to include any data processing device, such as a desktop computer, a laptop computer, a mainframe computer, an electronic notebook device, a computing server, a smart handheld device, or other related device able to process data. A module may also include, or be configured to access, computer-readable mediums and data storage devices or databases structures for storing different types of electronic data and instructions.

Each of the component modules can include programmed code, such as firmware or software instructions, for executing applications or programs that trigger a particular function of the module or earth model 300. In some implementations, the functions of a component module of the earth model 300, or application/program that corresponds to a module, is enabled by at least one of the geological reservoir models 260 (predictive models) described earlier with reference to FIG. 2. For example, the analytical rules encoded at the predictive models are used to perform data processing actions for an application that invokes the model, where the actions represent specific functions of an integrated model. In this manner, the earth model 300 may include multiple predictive models 264, 266, 268 that are integrated to form a single integrated multi-dimensional geological model.

As described later, the component modules of the earth model 300 are configured to provide different automated workflows that enable users such as geoscientists to accelerate subsurface characterization and field development processes relating to hydrocarbon exploration in a subterranean region. For example, the component modules and workflows enable users to accelerate as well as improve the accuracy of predicting reservoir properties that are indicative of subsurface hydrocarbon reserves. In some implementations, the accelerated and more accurate predictions about reservoir properties are generated ahead of a mechanical bit while drilling through an underground formation. For example, the predictions can occur in real-time concurrent with a geo-steering process of a well drilling operation.

Referring now to the component modules of FIG. 3, the earth model 300 generally includes a data storage module 302, a geological model project module 304, a model update module 306, and a formation selection module 308.

Module 302 is a digital data storage application that automatically manages and stores various types of data, including exploration data, plan development data, and interpretations of modelled data. In some implementations, the module 302 stores these different types of data in a standardized multi-dimensional format. For example, the standardized data storage format allows the earth model 300 and system 100 to support model analysis and information processing across the different dimensions of the datasets, including data structures that may be used by module 302 to store values and parameters of the datasets. In some examples, the module 302 interacts with data visualization tools of system 100 to pass information to other component modules of the earth model 300 and to enable visualization of modelled geological interpretations stored at module 302.

In at least one embodiment of the earth model 300, module 302 represents one or more multi-dimensional earth model data storage devices. For example, the module 302 can include (or be configured to access) at least one 3D earth model data storage (3DEMDS) that stores various types of data used by other component modules of earth model 300 to perform functions relating to hydrocarbon exploration. For example, the 3DEMDS is operable to store data used to generate respective two-dimensional or three-dimensional models for different subsurface areas of the earth.

The module 302 provides multiple types of outputs based on multiple types of received inputs. In some implementations, the module 302 processes received inputs and generates requested outputs in response to detecting event triggers that are based on event-driven programming encoded at the module 302 or earth model 300. For example, the module 302 can detect a first request to store a dataset, such as seismic data, at a storage device of the module 302, where the detected first request causes an event trigger for processing and storing a new dataset. Similarly, the module 302 can detect a second request to provide a dataset of seismic data stored at a storage device of the module 302, where the detected second request causes an event trigger for processing and transmitting a stored dataset to a requesting component or application of the earth model 300.

In response to detecting a received first request, the module 302 processes and stores the received dataset in accordance with parameters of the first request. In response to detecting a received second request, the module 302 processes and transmits the requested dataset in accordance with parameters of the second request. In some implementations, for the first request the module 302 processes or stores the received dataset based on formatting constraints specified by parameters of the first request, whereas for the second request the module 302 processes or retrieves the requested dataset based on formatting constraints specified by parameters of the second request. The respective formatting constraints of the first and second requests are analyzed by the module 302 with reference to a standardized multi-dimensional format used by module 302.

For example, parameters for the received (or requested) dataset can specify a formatting constraint indicating the dataset includes 3D digital data. In some examples, the parameters can specify items such as cell headers of a data structure used by the storage device of module 302, an X-location of a first data field or row element in the data structure, a Y-location of a second data field or column element in the data structure, a Z-location (depth) of the first or second data field along a depth dimension of the data structure, or a type indicator of the geological attributes that are included in the dataset. In some implementations, the data structure is based on a multi-dimensional tensor, a multi-dimensional matrix structure, various known database structures, or a combination of these.

In general, the earth model 300 can integrate event-driven programming across multiple component modules such that each module can: i) receive inputs or an in-bound request corresponding to an event trigger at the module that causes the module to perform a particular data processing function, ii) generate outputs or an output-bound request corresponding to an event trigger at another component module that causes the other module to perform a particular data processing function.

The geological model project (GMP) module 304 receives new datasets from several data sources relating to different geoscience disciplines. For example, the GMP module 304 receives datasets with data values and information that describe details about various field-stacked reservoir projects. In some examples, each of the data values and information are from different multiple datasets, where respective multiple datasets span each of the several disciplines, such as disciplines relating to well data, geophysical data, and geoscientific conceptual models.

The GMP module 304 generates multiple types of model related outputs based on multiple types of received inputs. In some implementations, the GMP module 304 processes received inputs and generates requested outputs in response to detecting event triggers that are based on event-driven programming encoded at the GMP module 304 or earth model 300.

For example, the GMP module 304 can detect a first request to provide a new set of seismic data values to the GMP module 304 for processing at the module 304, where the detected first request causes an event trigger at the GMP module for processing the new set of data values. In some implementations, the GMP module 304 is operable to obtain or generate requests to retrieve new datasets from other component modules based on iterative sequences for updating one or more predictive models of earth model 300. In some cases, the iterative update sequences can be dynamically controlled by system 100, based on a predetermined schedule set by system 100 for updating the analytical rules of the predictive models, or both.

The GMP module 304 processes the new set of data values to generate an output dataset for updating a particular predictive model of the earth model 300. The GMP module 304 can generate and transmit, to component modules of earth model 300, digital datasets that represent aspects of geological models (or full geological models) in response to an event trigger corresponding to a command of the iterative update sequence. In some implementations, the GMP module 304 is configured to execute integrated/iterative geological processes for performing one-dimensional data modeling, two-dimensional data modeling, and three-dimensional data modeling.

For example, the GMP module 304 can iteratively model properties and attributes of sedimentary facies for reservoir projects in different subterranean regions of the earth by integrating geological processes and datasets from different component modules of the earth model 300. The GMP module 304 is operable to generate results datasets for improving or optimizing performance of well placement programs and estimations about hydrocarbon reserves in a reservoir. In some implementations, the GMP module 304 generates updated 3D geological models that more accurately represent, in a digital format, different field reservoir geological bodies, reservoir and field performance forecasting estimates, hydrocarbon reserve estimations, and information describing uncertainty analysis. The GMP module 304 can also generate output datasets that indicate actual projected costs of individual reservoir characterization projects.

Model update module 306 ("module 306") is an automated and iterative workflow that is executed to ensure one or more of the multi-dimensional geological models of earth model 300 are kept up-to-date. For example, module 306 can iteratively execute automated workflows to provide new datasets of updated values as inputs to the predictive models to enhance or optimize the model's analytical, predictive, and control functions relating to well operation geo-steering.

In at least one embodiment of the earth model 300, module 306 represents a three-dimensional earth model update module. In some implementations, the module 306 is multidisciplinary and data driven update module that executes local scale model updates of existing partial- and full-field models based on optimization data collected around areas of newly drilled wells. For example, the module 306 can execute these local scale model updates based at least on optimization data collected by GMP module 304 or optimization datasets obtained from a storage device of module 302.

Module 306 can employ approaches that maintain and respect spatial continuity and geological correlations between sector areas and the partial- or full-field models. The model updates that are processed and executed using module 306 can include one or more of the structural as well as the petro-physical components of a particular multi-dimensional geological model of the earth model 300. Module 306 is configured to gain maximum value from the outputs of GMP module 304 as well as to maximize the optimization functions of the predictive models based on those outputs.

The formation selection module 308 is configured to automatically identify and select geological formation tops/surfaces using data from various well logs as well as other data sources of the system 100. The selected formation tops may be used as trainee wells or as candidate wells during drilling operations for hydrocarbon exploration. The formation selection module 308 includes an automated and iterative workflow that is executed to process and correlate data values of well logs for at least two vertical wells, two deviated wells, or combinations of each.

In some cases, the processing sequence of the workflow for the formation selection module 308 is based on processing and correlating data values for a training well with reference to data values for a nearby key master well. For example, the formation selection module 308 receives information for a training well along with well logs data associated with the training well. The formation selection module 308 also receives information and data values for the key master well. The data values of the key master well may indicate properties of the master well. The data values of the key master well are obtained from well logs and related geological events involving formation tops/surfaces that have been previously correlated.

Workflows of the formation selection module 308 are used to generate a model, such as a predictive model, that approximates potential patterns for correlating and matching the well logs of the key master and training wells. The predictive model generates model output results for both the key master and training wells using the processing schemes of the workflow. The formation selection module 308 is configured to automatically generate accurate selections of geological formation tops/surfaces for drilling one or more wells based on resulting outputs of the predictive model.

In at least one embodiment of the earth model 300, the formation selection module 308 represents a formation top auto picking (FTAP) module that is designed for automatically picking geological formation tops/surfaces using data values of well logs obtained from other component modules of earth model 300. In some implementations, the formation selection module 308 includes a predictive model that executes or applies a pattern recognition method against data values of the well logs as a technique to develop and refine its workflow automation processes for identifying and selecting geological formation tops/surfaces. For example, a predictive model 268 (model_N) can encode adaptive analytical rules for pattern recognition that are used to perform formation top auto picking based on data processing techniques executed by the FTAP module 308.

Model 308 is designed for automatically picking geological stratigraphic rock formation tops/surfaces using well logs. For example, the module 308 utilizes logging data for vertical or deviated wells to correlate with a nearby key master well and to perform the automatic picking. As discussed later, a pattern recognition method, applied to the well logs, is among the techniques considered in developing this automation process for picking formation tops. The key master well data includes describing geological events, such as event that correspond to formation tops/surfaces that have been properly analyzed by an expert. The trainee well with well logs data are also provided for processing using the workflow.

The workflow generates a model, such as the predictive model described earlier, that approximates the best possible patterns that correlate and match well logs of the key master, the trainee well, and any new well in the field. Geological formation tops/surfaces for trainee wells are automatically generated based on the resulting model (including model outputs), the prior wells, and the new well, accurate.

The earth model 300 further includes a smart well geo-steering (SWG) module 310, a well planning optimization (WPO) module 312, a well approval system (WAS) module 314, and a reservoir optimization module 316.

SWG module 310 is a technology tool for enhancing a geo-steering process performed using the earth model 300 and related sub-systems or components and devices of system 100. As used in this document, geo-steering is the intentional directional control of a well, such as a well being formed in the subterranean region of the earth. In some cases, the directional control can be based on the results of downhole geological logging measurements, three-dimensional targets in space, or combinations of each. The intentional directional control is generally used to ensure a directional wellbore stays within a zone or portion of a reservoir that is estimated to contain economically producible hydrocarbons. In some underground formations, geo-steering may be used to keep a wellbore in a particular section of a reservoir to maximize economic production from the well while minimizing gas or water breakthrough.

SWG module 310 is operable to accelerate the acquisition and processing of different types of data during well operation geo-steering. In general, well operation geo-steering is the analysis and use of real-time geologic, logging, sample, survey, and seismic data obtained during drilling of a wellbore to determine a position of the well bore in a subsurface area of an underground formation. In some implementations, the SWG module 310 provides data processing and analysis functionality that is an extension of the functionality provided by the formation selection module 308.

For example, the functionality of the SWG module 310 involves support for real-time automation of formation tops selection in horizontal wells and correlation with nearby wells. The SWG module 310 also includes an iterative automation workflow that is based on pattern recognition enabled by trained neural networks of predictive models integrated in earth model 300. The pattern recognition methods of the predictive models are applied to well logs to determine patterns and trends indicating relationships between data values or variables of the well logs.

The SWG module 310 is configured to receive real-time well borehole log data with a request to process the data using resources of the SWG module 310. The well borehole log data can include data values that specify well sector areas and indicate characteristics of geological reservoir bodies. In some implementations, the request causes an event trigger at the SWG module 310 that triggers processing of the data values for the well sector areas and geological reservoirs bodies. The SWG module 310 uses the pattern recognition methods of the predictive models to determine complex subsurface structural and textural patterns of geological areas and reservoir bodies.

The subsurface pattern outputs are used by the SWG module 310 to generate geological drilling instructions for conducting a geo-steering process. For example, the earth model 300 can use the drilling instructions to dynamically adjust the directional control of the wellbore to maximize production of hydrocarbons in a particular zone of a reservoir. In some implementations, the SWG module 310 is operable to use certain pattern recognition outputs of the predictive model as a main technique for developing the processing methods of its automation workflow. In some examples, the processing methods can include the generation and forward modeling of pseudo well logs and structural updates.

WPO module 312 is configured to optimize and automate an example well planning process. A workflow process executed using the WPO module 312 includes capturing and exploiting information that indicates uncertainty of reservoir properties to ensure maximum reservoir contact during a drilling operation. In some implementations, the uncertainty information is based on probabilistic modeling of reservoir quality relative to sediments and rocks of the reservoir, coupled with computed risk estimations of contacting low quality sediments. In some implementations, the uncertainty information is quantified in the form of a multi-dimensional risk volume or risk map that is based on probabilistic modeling using some or all of the geological, petrophysical, geophysical, and dynamic engineering data in system 100.

An application of the WPO module 312 can invoke or call a predictive model of the ML engine 250 to perform the probabilistic modeling. The WPO module 312 is operable to process and exploit the information derived from the probabilistic model to determine uncertainties relating to one or more properties of the reservoir. The WPO module 312 can use the uncertainties and information derived from the probabilistic model to determine planning parameters such as preferred geographic locations and resources of a well plan, including geo-steering parameters for improved directional control of drilling trajectories at the locations.

In some implementations, a predictive model 268 (model_N) called by the WPO module 312 encodes adaptive analytical rules for generating probability models that are used to perform functions related to constructing a well plan, enhancing an existing well plan, or optimizing a well planning process. The rules and functions can be invoked and managed respectively based on data processing techniques executed by the WPO module 312. In some cases, a fast marching method is applied to a 3D geological risk model to generate optimized well planning paths.

WAS module 314 is designed to enable timeline acceleration for obtaining approved well plans relative to prior approaches. For example, the WAS module 314 includes an iterative workflow that automates a well approval process and enables a rapid response to well drilling requirements. The timeline that can be accelerated includes the time required for entry of data associated with well data surveys to information for well types in a reservoir, all the way to the entry of data for multi-dimensional models to be used for the well planning.

The WAS module 314 can integrate multi-dimensional models of earth model 300 and well data obtained by different devices of system 100. For example, the WAS module includes a built-in flexible interface that allows for seamless integration of the multi-dimensional models and the well data. The integration can enable a project team to rapidly respond to one or more well drilling requirements.

Reservoir optimization module 316 allows users to efficiently test alternate scenarios relating to one or more reservoir models. The reservoir optimization module 316 is configured to efficiently test different reservoir model scenarios at least by executing one or more automated workflows. For example, the automated workflows can retrieve, execute, and step through requirements of an example test script constructed by a user to evaluate a model's accuracy in computing properties of different layers or sediments adjacent a section of a reservoir or the model's speed or precision when predicting hydrocarbon estimates for the reservoir.

The reservoir optimization module 316 is operable to provide a graphical user interface that enables the users to construct testing scenarios and provide user input for a scenario via the graphical interface. In some implementations, the user input defines testing parameters for evaluating a scenario against a particular reservoir model. The reservoir models can be multi-dimensional models, such as two dimensional or three dimensional models. Data representing the three-dimensional reservoir models is provided by a 3D earth model data storage (3DEMDS) device of the data storage module 302.

The reservoir optimization module 316 generates multiple types of model related outputs based on multiple types of received inputs. The reservoir optimization module 316 can process received inputs and generate requested outputs in response to an event trigger.

For example, the reservoir optimization module 316 can receive input data along with a request (that is, a user request) to test or evaluate a reservoir model against a particular scenario. The input data can include location parameters for a subsurface area of interest and information identifying a targeted reservoir in the area of interest. The input data can also include data related to multi-dimensional geological models that represent different field reservoir geological bodies, reservoir and field performance forecasting estimates, hydrocarbon reserve estimations, and information describing uncertainty analysis. The request may correspond to an event trigger at the reservoir optimization module 316 that causes the module to execute the test for evaluating the reservoir models.

The reservoir optimization module 316 generates optimized geological reports as outputs that quantify an uncertainty of hydrocarbon volumes for the areas of interest specified by the request. The input data for the reservoir models serve to quantify an uncertainty in hydrocarbon volumes. The uncertainty in hydrocarbon volumes quantified from the reservoir models can be used by the earth model 300 to determine more reliable reserve estimations and field development plans. In some implementations, the reservoir optimization module 316 communicates with the WAS module 314 to provide the uncertainty data for reference during the approval analysis of a field development plan or a well planning process.

In at least one embodiment of the earth model 300, the reservoir optimization module 316 represents a reservoir pore volume and economic optimization module (RPV&EO). In some implementations, the reservoir optimization module 316 evaluates a reservoir model to determine whether zones of a reservoir in an area of interest satisfy minimum criteria for porosity, permeability and hydrocarbon saturation, which can indicate a likelihood of maximizing economic production from the reservoir. The determination can be based on the RPV&EO features of the reservoir optimization module 316. In some examples, reservoir optimization module 316 is designed to empower users of earth model 300 and to efficiently and quickly test alternate three-dimensional or multi-dimensional reservoir model scenarios provided by data storage module 302. The reservoir optimization module 316 can quantify the uncertainty of hydrocarbon volumes, which results in more reliable reserve estimations and field delineation and development plans.

The earth model 300 further includes an exploration data module 318, a well data sources (WDS) module 320, a geophysical data sources (GDS) module 322, a resource cost assessment tools (RCAT) module 324, and a plans & resources module 326.

Exploration data module 318 is configured to implement a workflow that automatically manages, analyzes, optimizes, and stores large volumes of hydrocarbon field and reservoir data. The data may be collected in real-time in response to activities related to well/drilling operations (including logs, cores, or tests), seismic surveys, and analysis of seismic reflections. The data may be collected from various devices and modules of system 100.

The exploration data module 318 processes received inputs and passes requested outputs in response to detecting event triggers that are based on event-driven programming of module 318. For example, the exploration data module 318 can detect a request to store volumes of hydrocarbon data at a storage device of the module. The detected request causes an event trigger for analyzing the received data as well as managing and optimizing storage of new volumes of hydrocarbon data received by the exploration data module 318. In some implementations, the exploration data module 318 generates outputs describing the integration and optimization field reservoir real-time data, including geophysical data, collected and stored at the module 318.

The exploration data module 318 executes one or more of its workflow processes using data mining and business intelligence methods that leverage AI and ML technologies. For example, a data analysis and optimization program of the exploration data module 318 can invoke a predictive model of the ML engine 250 to perform statistical and stochastic analysis or modeling of the received hydrocarbon field and reservoir data. In some implementations, the statistical and stochastic approaches are employed to quantify, or precisely quantify, abnormal data conditions and data heterogeneity that can exists among the data values and variables of the received hydrocarbon data. The statistical and stochastic approaches can be used to perform data integration and to reduce uncertainty. In some examples, the uncertainty relates to whether a particular piece of data includes parameter values and information that is relevant or useful to a process of the earth model 300. The exploration data module 318 is configured to ensure consistent clean data is available to be utilized by the modules of the earth model 300.

WDS module 320 is a computing platform that enables earth model 300 to gain access to valuable well data and well data sources. The WDS module 320 can access the well data in real-time from various drillings rigs via satellite communication. The drilling rigs may be onshore drilling rigs, offshore drilling rigs, or both. In some cases, an example satellite communication channel is managed at the WDS module 320 to provide a data connection between modules of the earth model 300 and data processing resources of the onshore or offshore drilling rigs. In some implementations, the WDS module 320 is designed to bridge the gap between various well data formats that are used by different vendors. In particular, the WDS module 320 is configured to receive multiple sets of well data, where at least two sets of well data have distinct vendor-specific well data formats. The WDS module 320 is operable to apply one or more data standards across the sets of well data. For example, the WDS module 320 can use the one or more data standards to convert the respective vendor-specific formats to a standardized well data format. The WDS module 320 uses the standardized well data format to streamline and simplify the well data and to make data and related information more accessible by modules of the earth model 300.

The WDS module 320 generates model related outputs based on received inputs. For example, the WDS module 320 can process received inputs and generate requested outputs in response to an event trigger. For example, the WDS module 320 can receive input data corresponding to well data and information describing well data sources. The input data may comprise real-time well borehole data, including well header data, well drilling status information, well logs, datasets for various well and core samples, and information relating to well tests.

As described earlier, some or all of the input data may be received in a vendor specific format. An event trigger may be initiated at the WDS module 320 in response to the module receiving the input data. Initiation of the event trigger causes the WDS module 320 to process the input data to generate a modified dataset in the standardized format of the earth model 300. For example, the real-time well borehole data or well header data can be processed in accordance with an instruction for a data standard. The instruction is executed by the WDS module 320 to convert the well borehole data from a vendor-specific format to the standardized well data format used by the earth model 300.

GDS module 322 is a computing platform that enables earth model 300 to gain access to valuable geophysical data and geophysical data sources. The GDS module 322 includes functionality that is substantially the same as the functionality of the WDS module 320 described earlier, except that the GDS module 322 is specific to geophysical data, rather than well data. For example, the GDS module 322 can access the geophysical data in real-time from various geophysical crews and data acquisition devices via satellite communication. The geophysical crews and data acquisition devices may be onshore, offshore, or both. In some cases, an example satellite communication channel is managed at the GDS module 322 to provide a data connection between modules of the earth model 300 and data processing resources of the onshore or offshore geophysical crews and data acquisition devices.

In some implementations, the GDS module 322 is designed to bridge the gap between various geophysical data formats used by different vendors. In particular, the GDS module 322 is configured to receive multiple sets of geophysical data. At least two sets of the geophysical data can have distinct vendor-specific geophysical data formats. The GDS module 322 is operable to apply one or more data standards across the sets of geophysical data. For example, the GDS module 322 can use the one or more data standards to convert the respective vendor-specific formats to a standardized geophysical data format. The GDS module 322 uses the standardized geophysical data format to streamline and simplify the geophysical data and to make the data and related information more accessible by modules of the earth model 300.

The WDS module 320 is configured to pass the well data to exploration data module 318 such that a portion of the hydrocarbon data managed and stored by module 318 includes information and data values from the well data. Similarly, the GDS module 322 is configured to pass the geophysical data to exploration data module 318 such that a portion of the hydrocarbon data managed and stored by module 318 includes information and data values from the geophysical data.

RCAT module 324 includes applications that are configured to calculate projected costs of individual reservoir characterization projects. The RCAT module 324 can process received inputs and generate requested outputs in response to an event trigger. For example, the RCAT module 324 can receive input data along with a detected request to perform a cost assessment. The input data can include field performance reports and requirements, field/reservoirs datasets, and project costs of completed reservoir characterization studies. The input data can be received at least from the GMP module 304, the model update module 306, or the exploration data module 318.

The detected request can initiate an event trigger at the RCAT module 324 that causes the module to execute the cost assessment and generate a corresponding output that includes projected individual and total costs. In some cases, the cost of an individual reservoir characterization project is a portion of a total cost of integrated modeling services provided by the GMP module 304. The RCAT module 324 can sum the total costs of integrated one-dimensional, two-dimensional, and three-dimensional model services provided by the GMP module. In some implementations, the RCAT module 324 is configured to implement a workflow that automatically calculates individual and total costs for characterization projects and integrated model services.

Multi-dimensional geological models can include one or more components. The workflow executed by the RCAT module 324 incorporates delivered components of respective multi-dimensional geological models. The components can correspond to a number of tops, zones, core plugs, tests, and seismic traces. The applications and workflows of the RCAT module 324 allow project managers of a characterization project, or integrated model service, to estimate person-month costs for a discrete geoscience task and to compare the estimated costs with actual costs.

The RCAT module 324 includes a component for determining and comparing costs for different reservoir complexity levels. For example, the RCAT module 324 is operable to scan parameters or requirements of reservoir characterization projects to determine a respective complexity level for each of the characterization projects. The RCAT module 324 determines a cost estimate for a characterization project based on a respective reservoir complexity level for the project. The RCAT module 324 uses the component to compare the cost estimates for two or more for characterization projects across the different reservoir complexity levels.

The plans & resources module 326 is configured to provide processes that enhance performance of activities relating to hydrocarbon exploration. For example, the plans & resources module 326 provides applications for executing processes that enhance business performance of geoscience tasks, reservoir characterization projects, or field development plans. In some implementations, the plans & resources module 326 communicates with the RCAT module 324 to receive various types of requirements data as input data to process for enhancing or improving performance of a particular project or plan.

The plans & resources module 326 can receive short and long-range planning requirements, including budget, human resources, seismic acquisition, and drilling requirements. The plans & resources module 326 uses the received input data to identify geological project-level requirements that will satisfy business plan commitments and corporate metrics for expected economic production.

The plans & resources module 326 processes received inputs and generates requested outputs in response to an event trigger. For example, the plans & resources module 326 generates enhanced field and business performance reports as a requested output in response to processing the received inputs. In some implementations, the field and business performance reports outlines strategies for minimizing costs and maximizing revenues in the form of available resources to be converted to hydrocarbon reserves. Other embodiments relating to the plans & resources module 326 are described in more detail later with reference to FIGS. 13-16.

Figure 4:
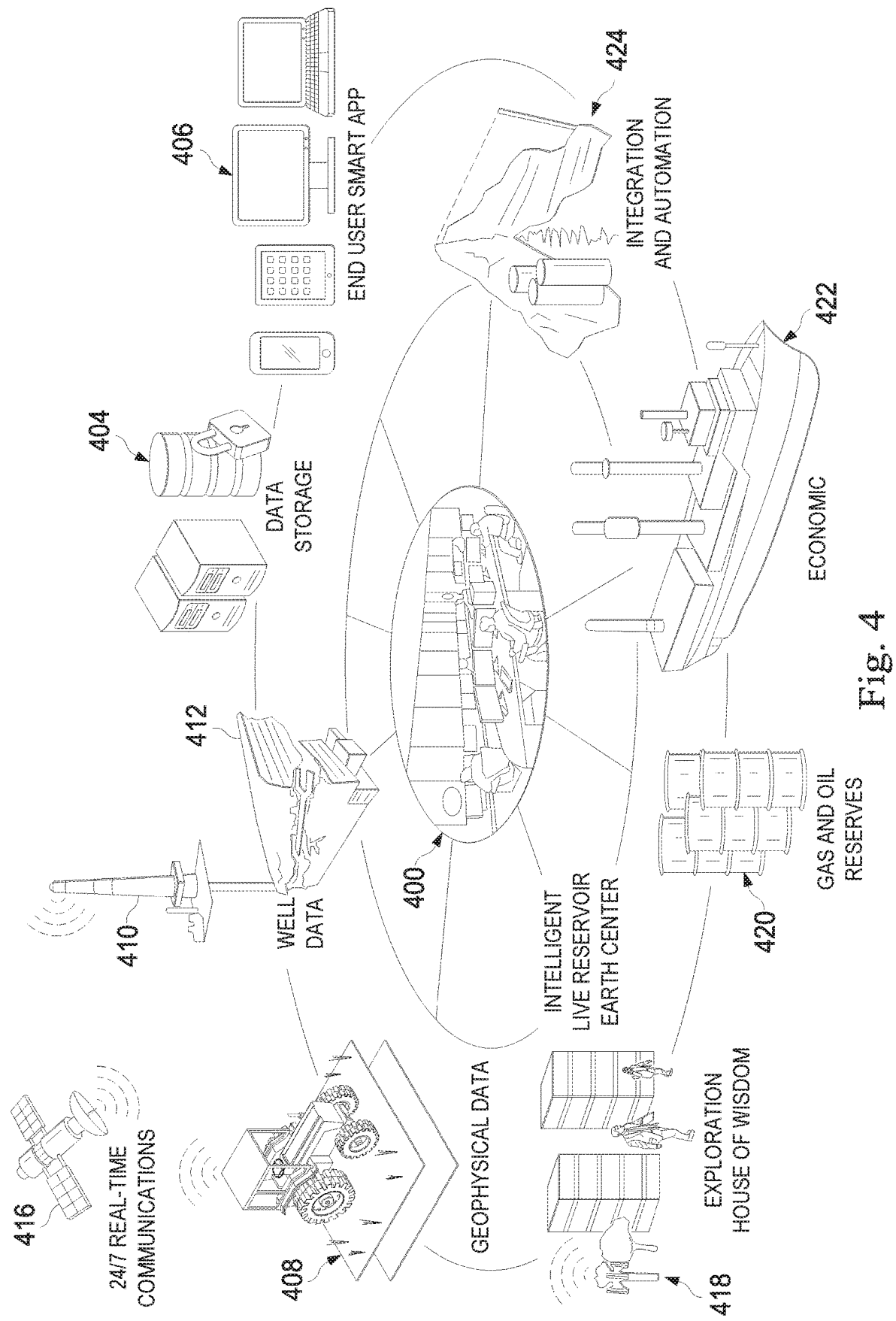
FIG. 4 illustrates an example operations center that communicates with systems and components used by oil and gas operators.

FIG. 4 illustrates an example operations center 400 that communicates with systems and components used by oil and gas operators. In some implementations, the operations center 400 is an extension of the control center 122 described earlier with reference to FIG. 1. In the embodiment of FIG. 4 the operations center 400 implements a reservoir Earth Model (REM) and is centralized relative to systems and devices of the operators. In some examples, the operations center 400 is at a location that is centralized relative to operator components and devices that are disposed at respective locations that are remote relative to the location of the operations center 400.

The operations center 400 interacts with one or more remote operator systems to execute various integrated and adaptive automation processes of the REM. The REM is an integrated multi-dimensional geological model that corresponds to the earth model 300 described earlier with reference to FIG. 3. The techniques described in this document provide an integrated process to automate the construction of multi-dimensional subsurface reservoir models that form the REM. Likewise, the techniques also provide an integrated process to automate the real-time updating of these multi-dimensional models.

An embodiment of the REM provides processes that adopt innovative self-modifying parametric (non-black box) approaches at least to perform the real-time updating of the models. In some cases the self-modifying parametric approaches are coupled with information derived from geoscience applications that integrate AI, ML, and big data analytics (BDA) technology. In other cases approaches employed by the REM are remote assembled processes that are centralized around a version of the REM that handles diverse, yet virtual, integrated adaptive automations. The process embodiment adopts novel self-modifying parametric (non-black box) approaches with original know-how in geoscience applications integrating AI, ML, and big data analytics (BDA) technology.

This remote assembled process is centralized around a reservoir Earth Model (REM), which handles the diverse yet virtual integrated adaptive automations. In some implementations, the Model 300 captures newly incoming data. The model 300 captures the newly incoming data irrespective of whether the data are applied per area, per field, or per reservoir. The earth model 300 selects one or more workflows that enable the model to obtain optimal results, such as results that have the lowest quantified uncertainty. The self-modifying parametric approaches are triggered in response to receiving new incoming data. In some examples, the new incoming data is received and processed in real-time. The workflow then updates the earth model 300 and its sub-models (or modules). This workflow process of updating the earth model 300 includes updating the older results with the new data.

The operations center 400 communicates with an example data storage 404. In some implementations, the data storage 404 corresponds to module 302 described earlier. For example, the data storage 404 can represent one or more multi-dimensional earth model data storage devices. In some examples, the data storage 404 includes data for instantiating a 3D earth model. The data storage 404 stores various types of data that can be used by other component modules of earth model 300 to perform functions relating to hydrocarbon exploration. For example, the data storage 404 is operable to store data used to generate multi-dimensional models for different subsurface areas of the earth.

In addition to the data storage 404, the operations center 400 communicates with multiple user applications 406. For example, the operations center 400 can include multiple networked client devices, such as tablets or laptop computers, which are each configured to access a suite of end user smart applications 406. In some implementations, each of the end user smart applications 406 corresponds to one or more of the modules that form REM, including the modules described earlier with reference to FIG. 3.

For example, the each of the end user smart applications 406 in the suite of applications may correspond to one or more of the smart well geo-steering (SWG) module 310, the well planning optimization (WPO) module 312, the well approval system (WAS) module 314, or the reservoir optimization module 316. In some implementations, each of the applications are operable to provide graphical user interfaces that enable users to execute various functions that are encoded as instructions in the application. For example, at least one of the user applications 406 can provide a graphical interface to update and view real-time information broadcasted from drilling rigs.

The operations center 400 also communicates with geophysical data acquisition devices 408. The operations center 400 can receive geophysical data, in real-time, from devices 408 via satellite systems 416. In some implementations, a satellite communication channel managed at the GDS module 322 of the REM provides a data connection between other modules of the REM and data processing resources of the onshore or offshore geophysical crews and data acquisition devices. For example, the devices 408 may be used by geophysical crews and can represent data acquisition devices that are onshore, offshore, or both. The system 100 uses the geophysical data received from devices 408 to populate database structures of the GDS module 322 with valuable geophysical data and information that describes various geophysical data sources.

The operations center 400 also communicates with well data acquisition devices 410. The operations center 400 can also receive well data, in real-time, from well data sources (that is, devices 410) via satellite systems 416. In some implementations, a satellite communication channel is managed at the WDS module 320 of the REM to provide a data connection between other modules of the REM and data processing resources of the onshore or offshore drilling rigs. For example, the devices 410 can represent drilling rigs that are onshore drilling rigs, offshore drilling rigs, or both. The system 100 uses the well data received from devices 410 to populate database structures of the WDS module 320 with valuable well data and information that describes various well data sources. The well data may be descriptive of characteristics and properties of a well bore in a particular subterranean region or geological area 412.

The operations center 400 also communicates with devices or systems of an example exploration house of wisdom 418, devices that store or process information pertaining to oil and gas reserves 420, economic datasets 422, and devices that execute one or more integration and automation workflows 424.

The exploration house of wisdom 418 ("E-HoW 418") provides an embodiment of the exploration data module 318 that is used to perform one or more functions of module 318. For example, the E-HoW 418 can represent an automated central network that is operable to manage, analyze, optimize, and store datasets representing hydrocarbon fields and reservoirs as well as real-time well and seismic data. In at least one example, the datasets include the real-time geophysical data received from the geophysical data acquisition devices 408 and the real-time well data received from the well data acquisition devices 410.

In some implementations, the E-HoW 418 is an automated central network of storage devices. The networked storages devices may be managed collectively by control logic of a predictive model that is based on AI and ML technologies. Based on the control logic, the predictive model is operable to execute workflows to automatically manage the processing, optimization, and distribution of the received datasets for storage across the network of storage devices. In some instances, the predictive model is trained and operable to invoke statistical and stochastic analysis when processing datasets for optimization and storage.

For example, an optimization approach can include processing parameters, including parameter values, of a dataset generated during a well drilling operation. The optimization approach can also include detecting certain missing and abnormal parameters or parameter values corresponding to a well bore and properties of geological layers along the drilling trajectory. The approach may further include performing one or more mathematical processes, such as data imputation, to predict different parameters and parameter values that correspond to the drilling operation so as to optimize the generated datasets for storage at a particular storage device associated with E-HoW 418.

The datasets stored at the E-HoW 418 can also include at least a portion of the information pertaining to oil and gas reserves 420. In some examples, the information pertaining to oil and gas reserves 420 describes various known or suspected locations for obtaining trapped hydrocarbon accumulations. The information can be used by modules of the earth model 300 or REM to predict some (or all) geological-related factors to bring the hydrocarbons (oil and gas) to the surface at optimum or threshold cost. The economic datasets 422 includes data describing economically producible hydrocarbons. In some implementations, the data of the economic datasets 422 that describes the economically producible hydrocarbons is based on different sets of information pertaining to oil and gas reserves 420.

As indicated earlier, the operations center 400 communicates with devices, modules, components, or sub-systems that are involved in the execution of integration and automation workflows 424 of the REM. In this context, the operations center 400 can represent a subset of modules that form a centralized portion of the REM, which may be described generally as a central REM.

Each of the integration and automation workflows 424 utilizes real-time input and output data connected with the multiple modules (that is, the thirteen modules of FIG. 3) of the REM that represent digital analytical resources and multiple sampling sensors. For example, at least a portion of the data pertaining to logging while drilling and real-time geo-steering of wells can be implemented as a wireless loop between offshore and onshore drilling rigs and the central REM. In some implementations, each workflow 424 in one or multiple automated processes is composed of a set of complex tasks that feed another connected workflow. These workflows seamlessly relay results of their respective operations back to the central REM.

The central REM is an system that adds or provides adaptive automation and integration 424 to some (or all) subordinate or "child" workflows executed by the individual modules of earth model 300. In some implementations, the central REM is operable to integrate or assemble the workflows together into a single, multiple user parallelized interface. For example, this single interface can be configured to list interactive options to be used by exploration professionals to implement occasional manned intervention and human expert supervision of the REM. The single, multiple user parallelized interface is configured to provide the interactive options for implementing the human intervention and expert supervision of the REM without halting any particular sub-component of an integrated process.

Figure 5:
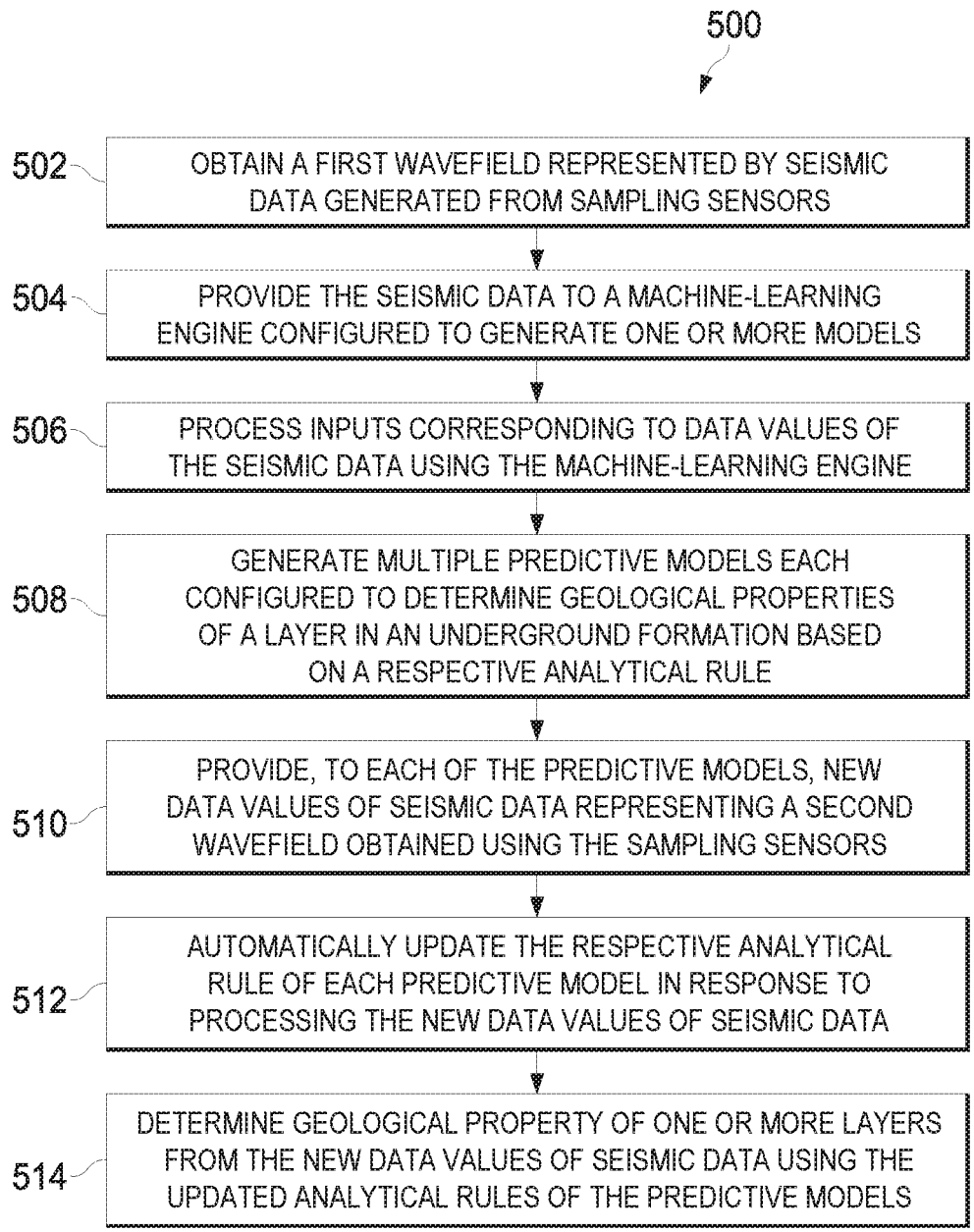
FIG. 5 is a flow diagram of an example process for identifying hydrocarbon reserves of a subterranean region using a reservoir earth model.

FIG. 5 is a flow diagram of an example process 500 for identifying hydrocarbon reserves of a subterranean region using a reservoir earth model. Process 500 can be implemented or executed using the system 100. Hence, descriptions of process 500 may reference the computing resources of system 100 described earlier in this document. In some implementations, steps or actions of process 500 are enabled by programmed firmware or software instructions, which are executable by one or more processors of the devices and resources described in this document.

Referring now to process 500, the system 100 obtains a first wavefield represented by seismic data generated from multiple sampling sensors (502). A subset of the sampling sensors can be geophones or other related sensors that are deployed in the subterranean region. For example, the sampling sensors may be deployed for conducting field operations associated with development and production of resources such as oil and gas from the subterranean formation 100, described earlier. As described later, the seismic data may be obtained iteratively and used to identify geological surfaces in the subterranean region or for performing simulation, planning, and optimization of production operations of a wellsite systems.

At least a portion of the seismic data is provided to a machine-learning engine of the system 100 for analysis and processing using the machine-learning engine (504). For example, data values of the seismic data that indicate or describe properties of underground formations in the subterranean region are provided as inputs to data models of the ML engine 250. The data models may be untrained ML models corresponding to artificial neural networks that are used by the ML engine 250 to generate one or more predictive models. For example, the ML engine 250 is operable to generate a predictive model based on a training phase executed by system 100.

The system 100 processes the inputs corresponding to data values of the seismic data using the machine-learning engine (506). For example, the system 100 includes an AI data processing system (represented by the computing device 200) that is used to generate predictive models for modeling characteristics of the subterranean region. The AI data processing system is operable to generate multiple predictive models in response to processing information or datasets, such as information obtained by a variety of data acquisition devices, stored at the system 100. In some implementations, to generate the predictive models, the AI data processing system causes the ML engine 250 to execute a training phase in which input data values of an example training data set are processed at one or more of the ML models to generate one or more predictive models.

The system 100 generates multiple predictive models in response to processing input data values of seismic data (508). Each predictive model is configured to determine geological properties of layers, sections, or reservoirs of the underground formation based on a respective analytical rule of the predictive model. In some implementations, the analytical rule is encoded at the model and continuously adapted and improved based on the AI and ML technologies of the ML engine 250. In some cases, the analytical rule is encoded at the model as software instructions for carrying out data processing techniques of an application program or computing module that corresponds to the model.

The input data values used to generate the models may be a feature set of values from the training data set. The training data set may be formed from the seismic data representing the first wavefield that was captured using the geophones or other related sensors deployed in the subterranean region. Feature values of the training dataset can be generated using different mathematical computations for deriving features. In some implementations, features or feature values of a training dataset for modeling geological properties can be derived using various techniques of a feature learning process, such as correlation analysis, variable clustering, or variable importance lists from decision trees, as well as techniques related to random feature selection.

For the machine learning aspects of process 500, feature learning can be a sub-process involving a set of techniques that allows the AI data processing system to automatically discover representations needed for feature detection or classification from raw data. For example, the feature learning can be an automated process (replacing manual feature engineering) that allows a machine to both learn a set of features and use the features to perform a specific task. In some examples, the specific task can involve training a neural network of ML engine 250 to model, detect, infer, or otherwise predict geological properties and other characteristics of items (a physical item) in a subterranean region.

New data values of seismic data are provided to each of the generated predictive models (510). For example, new data values of seismic data representing a second wavefield obtained using the subset of sampling sensors deployed in the subterranean region are provided to each of the generated predictive models. In some implementations, the input data values of the training data set processed at the ML engine 250 to generate the predictive models correspond to a first iteration of seismic data obtained for the training phase of system 100, whereas the new data values of seismic data representing the second wavefield may be derived or extracted from a second iteration of seismic data obtained during an implementation phase of system 100.

In some examples, a respective subset of new data values may be derived or extracted from the second iteration of seismic data for each predictive model based on the particular functionality or analytical rules that are encoded at the predictive model. For example, the system 100 is operable to determine that a predictive model 264 (model_1) encodes a set of adaptive analytical rules that are used to perform functions related to formation top auto picking based on data processing techniques executed by the FTAP module 308.

The system 100 is operable to scan, read, or otherwise analyze discrete variables and parameter values of the second iteration of seismic data. In response to analyzing the variables and values, the system 100 is operable to determine or locate variables and parameters that are often used for module functions such as identifying and selecting formation tops. For example, the system 100 can determine that, in the second iteration of seismic data, certain variables and parameters of the well logs are routinely processed at the FTAP module 308. This example the FTAP module 308 uses the predictive model 264 (model_1) to automatically select or pick certain geological formation tops/surfaces based on input criteria from a user.

In some instances, the system 100 is operable to parse the second iteration of seismic data to locate well logs or log data related to certain types of wells, such as vertical or deviated wells. The system 100 is operable to form a subset of new data values based on information that is parsed or extracted from the well logs. For example, the parsed information can include discrete variables and parameter values that describe attributes of deviated wells. The system 100 provides the subset of new data values to at least model_1 of the ML engine 250 for further processing at the model_1. For example, the system 100 can provide the subset of new data values derived from the second iteration of seismic data based on the feedback loop 270.

The system 100 is configured to automatically update the respective analytical rule of each predictive model in response to processing the new data values of seismic data (512). For example, each of the respective subsets of new data values that are derived from the second iteration of seismic data are processed at its corresponding predictive model to update, enhance, or otherwise optimize the particular functionality and analytical rules encoded at the predictive model. Referring to the above example involving the FTAP module 308, a subset of new data values that are extracted from the well logs are processed at model_1 to optimize or enhance a predictive capability of the model.

The discrete variables and data values describing attributes of deviated wells may be processed through layers of the model's neural network to update or tune biases and weights of the neural network. In general, these biases and weights of the model's neural network contribute to the model's accuracy in generating certain predictions and inferences that are used to identify and select geological formation tops/surfaces. For predictive models that are developed from trained neural networks, the adaptive analytical rules of the predictive model are generally based on the tuned biases and weights of the model's neural network. In this manner, processing new data values of seismic data to tune the biases, weights, and related features of the model's neural network can trigger a corresponding update to the adaptive analytical rules encoded at the model.

The system 100 is configured to determine a respective property of one or more layers in an underground formation from the new data values of seismic data using the updated analytical rules (514). In some implementations, system 100 is configured to determine (i) a first geological property of a layer using the updated analytical rule of a first predictive model (model_1) and (ii) a second, different geological property of the layer using the updated analytical rule of a second, different predictive model (model_2).

For example, one or more neural networks of model_1 and model_2 can process respective subsets of data values that are extracted from subsequent iterations of seismic data that indicate new details about attributes, characteristics, and properties of the subterranean region. In some examples, a first subset of data values indicates new details about attributes and properties of layers in the underground formation of the subterranean region, whereas a second subset of data values indicates new details about characteristics and properties of deviated wells in the subterranean region.

In response to model_1's processing of the data values in the first subset and model_2's processing of the data values in the second subset, the AI data processing system is operable to update or optimize the respective analytical framework for each of model_1 and model_2. In some implementations, the analytical rules encoded at each of model_1 and model_2 can be used or invoked by the FTAP module 308 to detect different types of layer properties in an underground formation for determining suitable locations to form deviated wells in a subterranean region. For example, a predictive model's analytical rules may be optimized by enhancing the model's accuracy in predicting that an identified geological formation top that is selected for well drilling will lead to a particular amount of hydrocarbon being extracted from a reservoir in the region.

Figure 6:
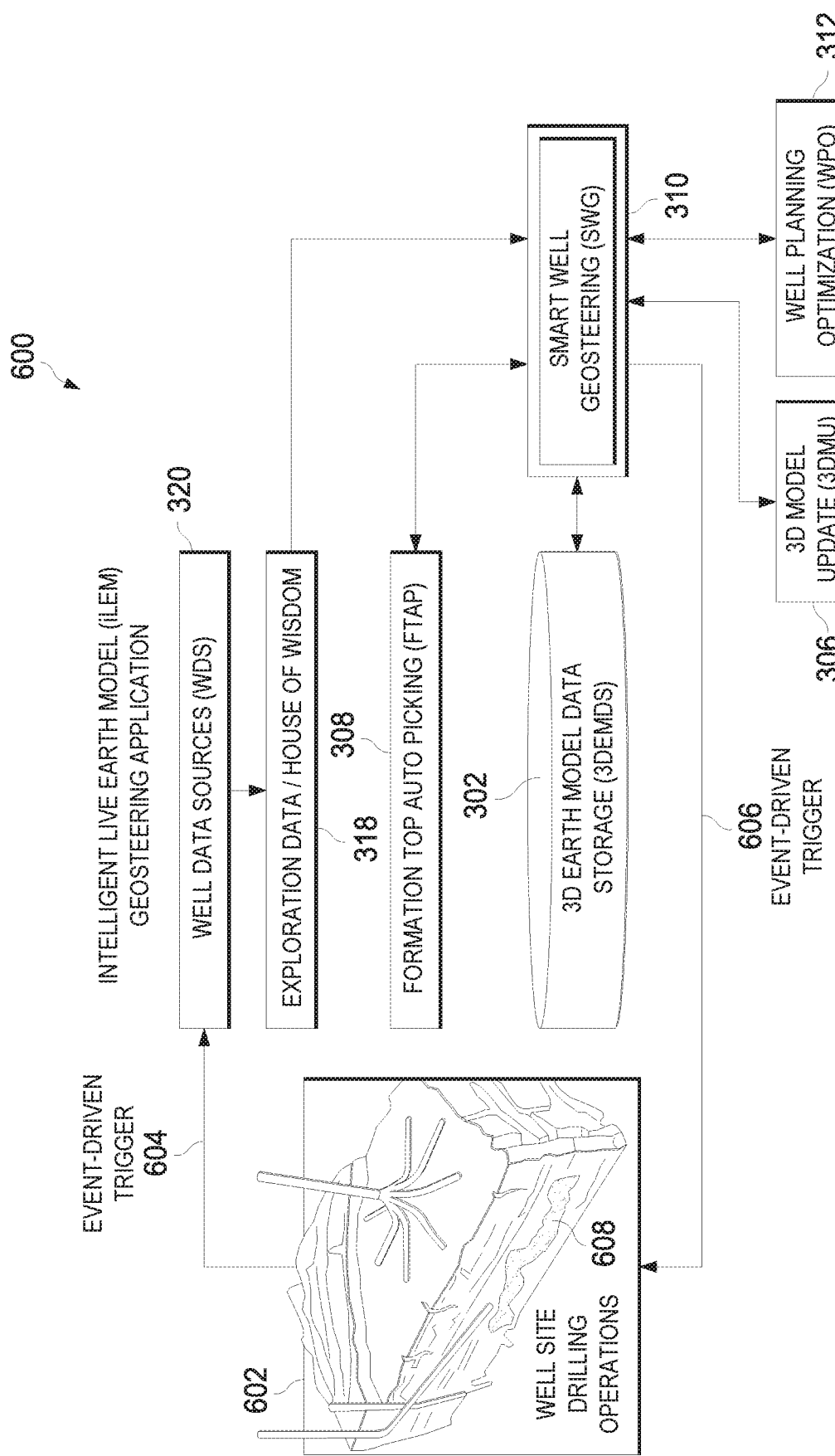
FIG. 6 is a block diagram of an example geo-steering application.
Figure 7:
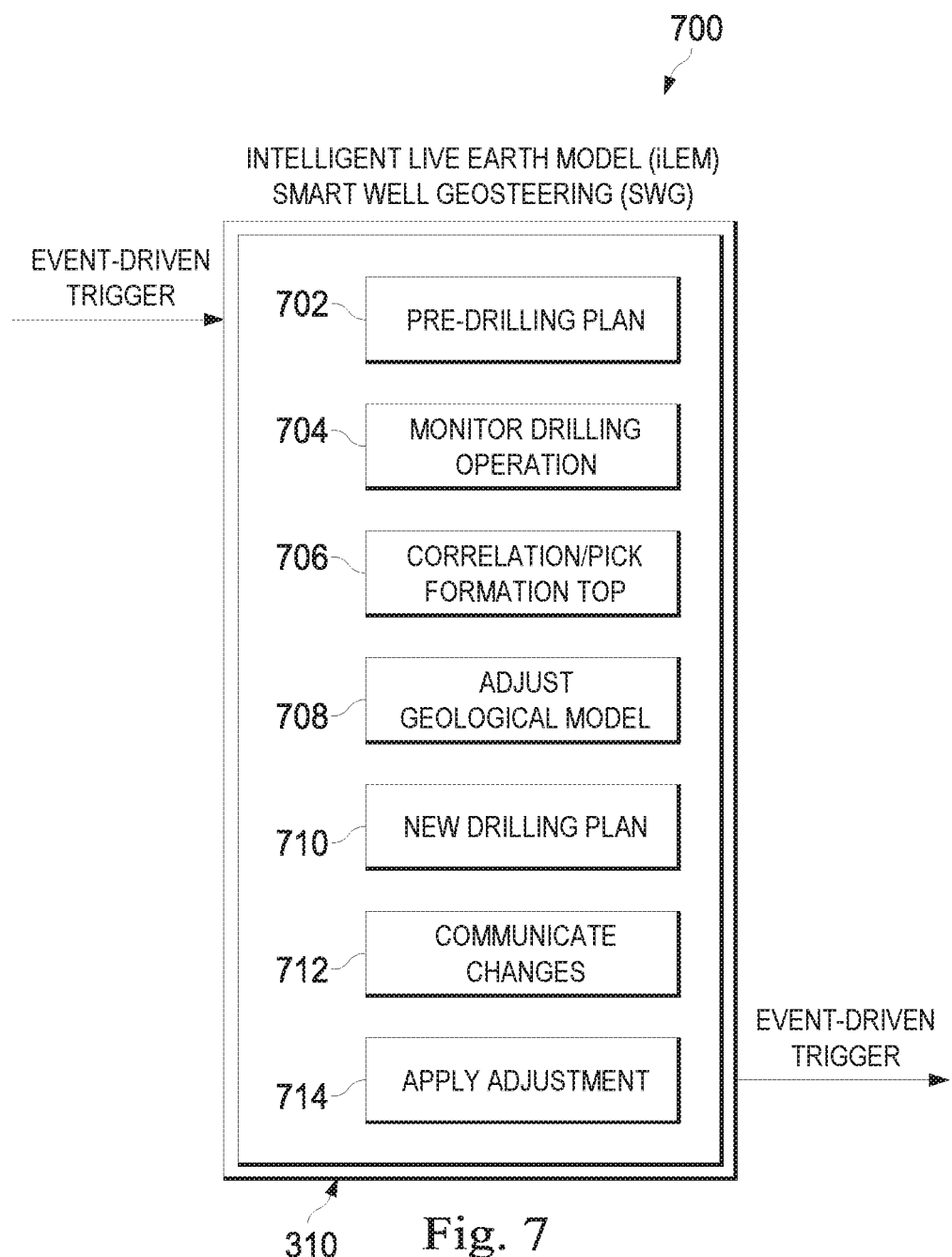
FIG. 7 is a flow diagram of an example smart well geo-steering process.

FIG. 6 is a block diagram that shows an example geo-steering application 600, including an example set of modules that cooperate to provide one or more functions of the geo-steering application 600. Relatedly, FIG. 7 is a flow diagram of an example smart well geo-steering process 700 that can be implemented using the geo-steering application 600 of FIG. 6.

In general, well operation geo-steering is the analysis and use of real-time geologic, logging, sample, survey, and seismic data to at least determine the position of a well bore in a subsurface area of an underground formation. The various types of data relating to the well operation geo-steering may be obtained in real-time during an example drilling operation. The data can be used to modify an existing well plan while drilling to optimize a position of the well within a reservoir section of the underground formation to achieve certain well objectives.

This process involves analytical supervision and control of directional drilling activities of a well trajectory. The implementation of the smart well geo-steering process 700 provides exploration and reservoir development teams with techniques that allow for the improved placement of wells in target reservoirs. The analytical controls relative to directional drilling and improved placement of the wells can allow for more effective production hydrocarbons for conversion to oil and gas.

In some cases, the enhanced effectiveness in the oil and gas production can be based in part on the geo-steering application's ability to provide continuous (that is, 24/7) monitoring of well operations as well as improved data communications between the various computational resources that are involved in the control and monitoring of the well operations. The well operation geo-steering techniques which pertain to the geo-steering application 600 also involve setting standards of work processes, including establishing and institutionalizing best practices that allow for better manpower utilization relative to prior approaches.

A sample operation will be described to illustrate the smart well geo-steering process 700 with reference to the embodiment of FIG. 6. In the example embodiment of FIG. 6 the sample operation is a well site drilling operation 602.

The smart well geo-steering process 700 includes receiving input data corresponding to a pre-drilling plan in response to an event-driven trigger 604 that also causes processing of the received input data (702). For example, the pre-drilling plan can define an example drilling operation to be performed in particular subterranean region. In some implementations, the event-driven trigger corresponds to the trigger functions of the smart well geo-steering (SWG) module 310 described earlier with reference to FIG. 3.

The geo-steering application 600 monitors one or more drilling operations (704). For example, the drilling operation can include drilling through various types of rock formations to form one or more wells. In some examples, the pre-drilling plan representing the input data is received as a dataset from the 3DEMDS module 302, whereas the data related to monitoring the drilling operations is generated by well data sources (well data acquisition devices 410) and received at the geo-steering application 600 via the exploration data module 318 or E-HoW 418.

The geo-steering application 600 executes processes for formation top correlation and automatically picking geological formation tops at least based on information obtained in response to monitoring the drilling operations (706). For example, when a well is drilled actual formation tops may be correlated across a geological area and used to select a pick location based on methods executed by FTAP module 308. In some implementations, the formation tops correlation and picking is performed based on methods such as rate of penetration (ROP) charts, formation cuttings, and sediment logging.

The geo-steering application 600 uses the information obtained in response to monitoring the drilling operations and the methods for formation tops correlation and picking to adjust and update one or more geological models of the REM, such as the integrated multi-dimensional geological earth model 300 described earlier (708). For example, module 306 can iteratively execute automated workflows to cause new datasets of updated values relating to the drilling operations to be provided as inputs to predictive geological models of the geo-steering application 600. The new datasets of updated values are provided to enhance or optimize the geo-steering application's analytical, predictive, and control functions relating to well operation geo-steering.

In some implementations, the geological models are updated to adjust different analytical rules employed by the model. For example, a predictive model of the REM can be updated to perform processes related to reservoir characterization that involve interpreting data gathered at spatially sparse wells, in addition to limited bandwidth seismic data. In some examples, the seismic data is gathered from obtaining multiple wavefields in response to drilling the subterranean region to penetrate one or more layers in an underground formation of the region.

The geo-steering application 600 uses the adjusted (or updated) predictive and analytical capabilities of the geological model to generate a new drilling plan (710). The new drilling plan can be based on predictions about geological-related factors for accurately locating trapped hydrocarbon accumulations. For example, the new drilling plan can be based on detailed prediction of about subsurface properties such as rock porosity, permeability, hydrocarbon distribution, and water saturation at each discrete element of a reservoir. The new drilling plan and bring the hydrocarbons (oil and gas) to the surface within a threshold cost or economic production metric.

The geo-steering application 600 communicates changes to an existing drilling plan based on the new drilling plan (712). The geo-steering application 600 is operable to generate commands for either applying the adjustment to the geological models, as described earlier, or applying an adjustment to drilling trajectories of a current drilling operation based on control parameters of a new drilling plan (714). For example, the geo-steering application 600 is operable to generate geological drilling instructions, including commands and event-driven triggers 606 for controlling devices and equipment used to conduct a geo-steering process. The REM can use the drilling instructions to dynamically adjust directional controls of a wellbore to maximize production of hydrocarbons 608 in a particular zone of a reservoir.

The geo-steering process can involve obtaining certain key components of a reservoir model, such as structural framework and rock textual properties. These components are among the constituents that can vary significantly at different locations within a single reservoir. Because reservoirs are deep under the surface of the earth, these components can be measured directly only at boreholes where wells have been drilled and properties monitored. Direct measurement techniques of monitoring the properties can include coring and electric logs that are run in wells and analysis of core samples of rocks obtained from the wells.

Figure 8:
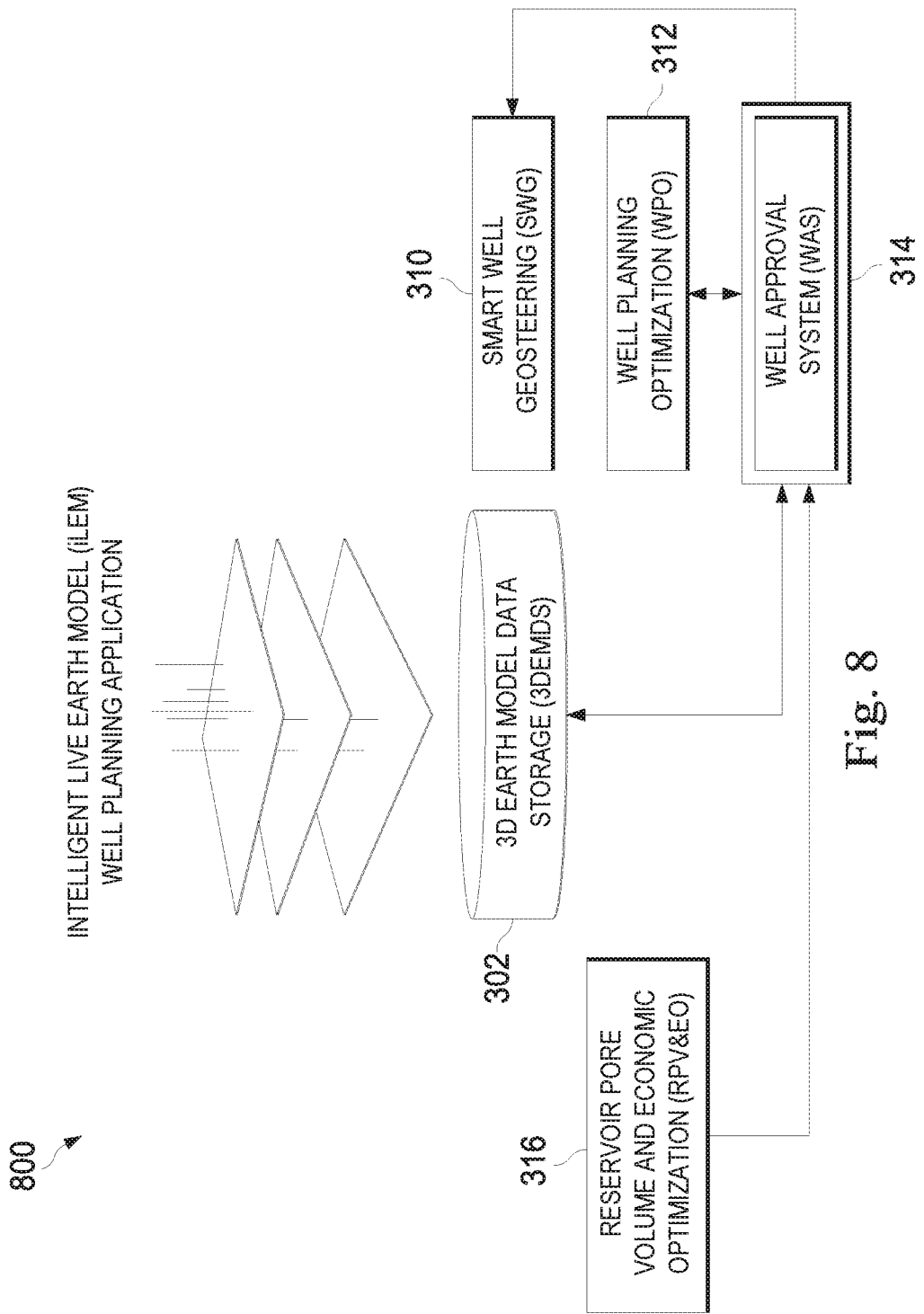
FIG. 8 is a block diagram of an example well planning application.
Figure 9:
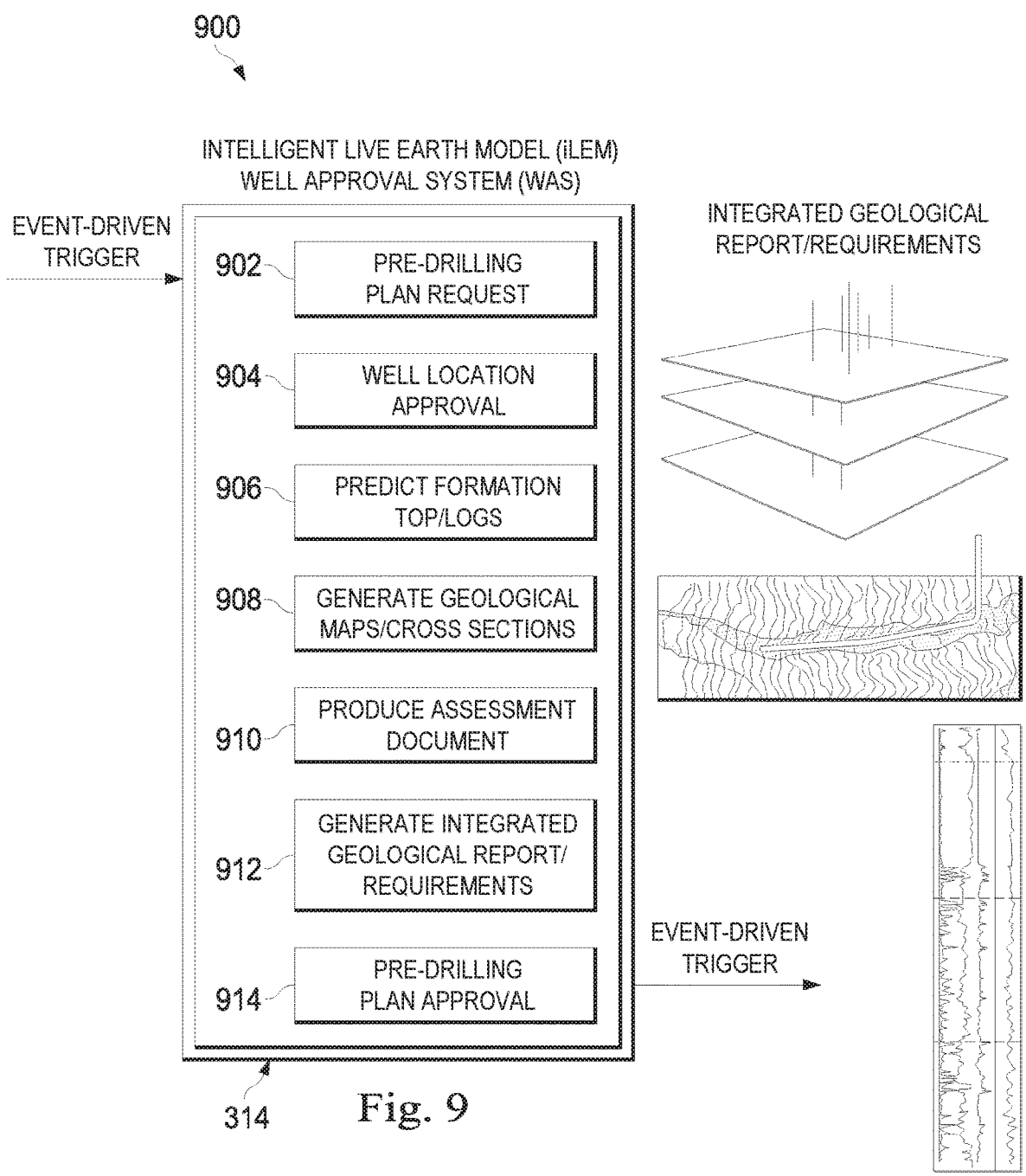
FIG. 9 is a flow diagram that includes steps of an example process of a well approval system.

FIG. 8 is a block diagram that shows example modules of a well planning application 800. Relatedly, FIG. 9 is a flow diagram that includes steps of an example process of a well approval system 314 that includes, or that is based on, the well planning application 800 of FIG. 8. The well planning application 800 can represent an automation tool of the well approval system 314 in the example of FIG. 9. The well planning application 800 is developed to be part of the REM, such as embodiments of the REM that correspond to the earth model 300.

The well approval system 314 and well planning application 800 are configured to improve the efficiency of drilling operations relative to prior approaches. For example, the efficiency of the drilling operations may be improved from the planned well survey input phases to the generation of final reports. The automation tool of the well approval system 314 can be used to gain maximum value from reservoir characterization. For example, the tool displays information such as forwarded logs, cross sections, average reservoir properties, and risk maps extracted from geo-cellular models. The models may be highly integrated and up-to-date 3D or multi-dimensional geo-cellular models.

The automation tool is operable to incorporate the information extracted from the models in an integrated geological report and requirements document rapidly relative to prior approaches. For example, the tool is able to incorporate certain information sets within time thresholds of one to two minutes. In general, the automation tool of the well approval system 314 provides various options for process optimization, higher levels of efficiency, and enhanced manpower utilization. These options are just some of the benefits that can be realized through the techniques afforded by the automation tools of the well approval system 314.

A sample operation will be described to illustrate the example process 900 of the well approval system with reference to the embodiment of FIG. 8.

The well planning application 800 provides a workflow that automates a well approval process 900 to enable a quick or rapid response to well drilling requirements. In some cases the requirements can be received as input data corresponding to a pre-drilling plan request in response to an event-driven trigger that also causes processing of the received input data (902).

For example, a first portion of the data corresponding to the pre-drilling plan request can be received from the reservoir optimization module 316. This first portion of the data can include new well headers, including X-location and Y-location, well survey data, and information describing targeted reservoirs. A second, different portion of the data corresponding to the pre-drilling plan request can be received from the 3DEMDS module 302. This second portion of the data can include 3D geological models that represent, in digital format, the field/reservoirs geological bodies, reservoir and field performance forecasting, hydrocarbon reserves, and uncertainty analysis.

The well planning application 800 generates well location approval (904). The well planning application 800 can generate the well location approval based on input data that includes location parameters for a subsurface area of interest and information identifying a targeted reservoir in the area of interest. For example, the well planning application 800 may generate a well location approval based on results computed by the reservoir optimization module 316 in response to evaluating a reservoir model against a particular scenarios that involve drilling operations for the targeted reservoir.

The well planning application 800 computes predictions about formation top/logs (906). For example, the predictions about formation top/logs are computed with respect to the target reservoir. The well planning application 800 generates geological maps and cross sections for one or more areas of interest based on data describing the location parameters of a targeted reservoir (908). The well planning application 800 produces various types of assessment documents that are related to approving or disapproving of a particular well plan (910). For example, the well planning application 800 can process information derived from probabilistic models WPO module 312 to determine uncertainties relating to properties of the targeted reservoir. The well planning application 800 can reference uncertainties derived from the probabilistic model to determine planning parameters (numerical parameters), including preferred geographic locations and resources that are required for a well plan to meet or exceed an example approval threshold.

The well planning application 800 generates integrated geological reports and requirements which are relevant to approval of a well plan (912). The well planning application 800 is configured to provide an indication of approval with regard to the pre-drilling plan request provided as input to (914). In some implementations, the well planning application 800 is operable to generate geological well drilling reports. In addition to the geological well drilling reports, the well planning application 800 is operable to generate predictions relating to well formation tops, reservoir properties, and geological uncertainty relating to uncertainty of hydrocarbon volumes in a particular areas of interest as defined by the pre-drilling plan request.

Figure 10:
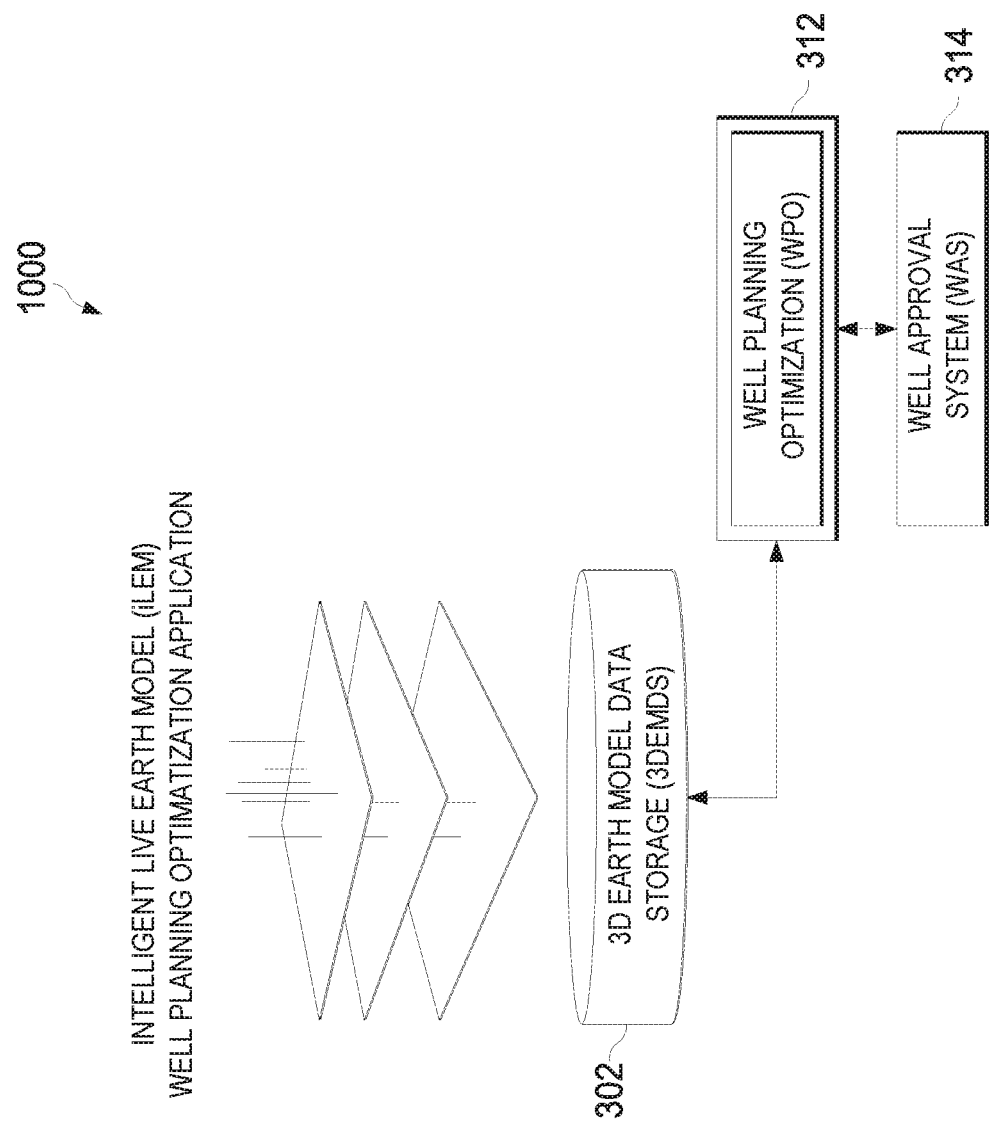
FIG. 10 is a block diagram of an example well planning optimization application.
Figure 11:
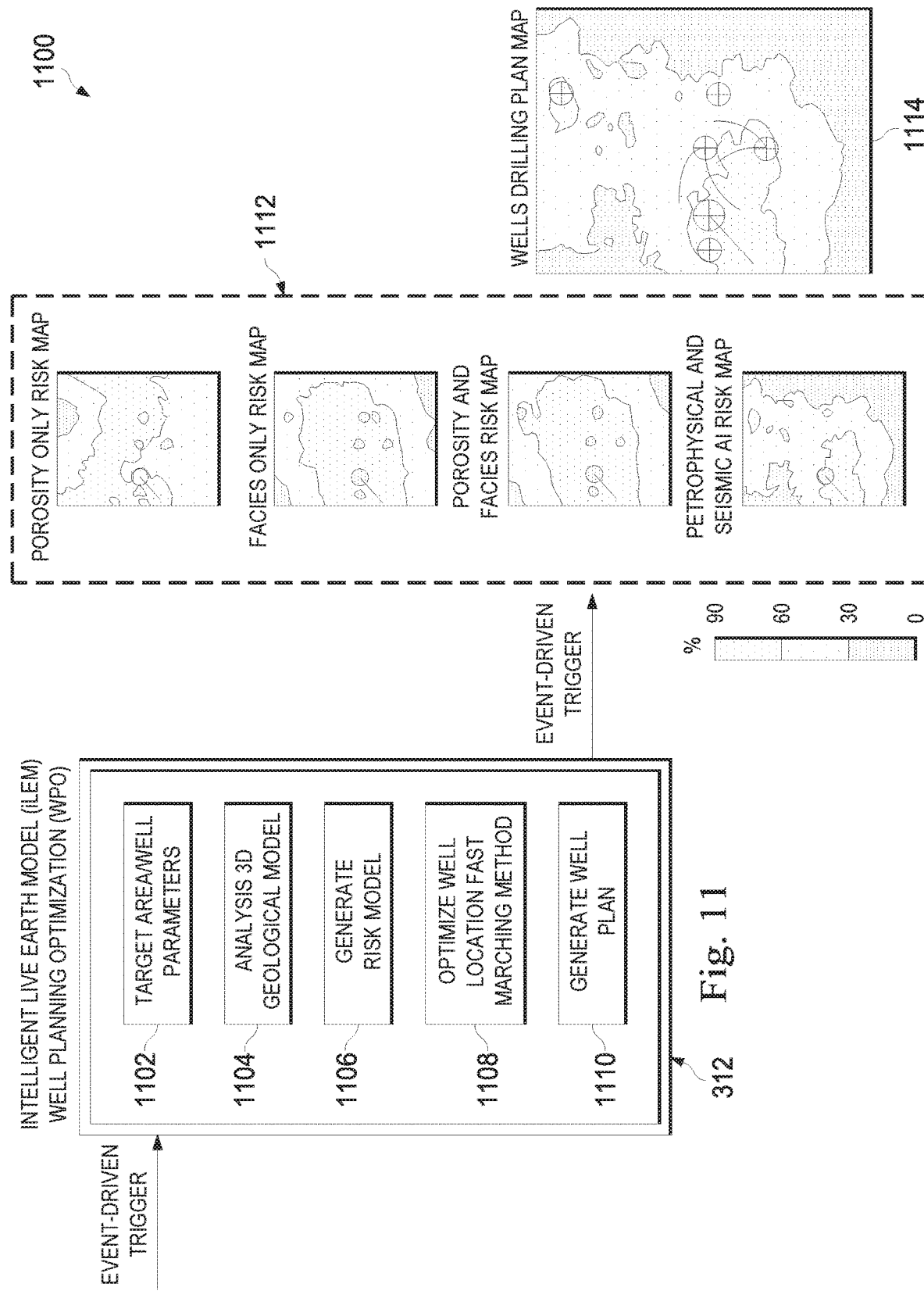
FIG. 11 is a flow diagram of an example process associated with optimizing a well planning operation.

FIG. 10 is a block diagram that shows example modules of a well planning optimization ("WPO") application 1000. Relatedly, FIG. 11 is a flow diagram of an example process 1100 associated with optimizing a well planning operation. The WPO application 1000 provides well planning optimization methods for optimizing and automating one or more well planning processes, such as the process 1100 in the example of FIG. 11. Additionally, the WPO application 1000 provides an automated process that is operable to optimize well planning and placement based on the integration of static and dynamic data, including information pertaining to reservoir uncertainty, to maximize reservoir contact during drilling operations.

A sample operation will be described to illustrate the example process 1100 of the well optimization application 1000 with reference to the embodiment of FIG. 10. In the example embodiment of FIG. 10, the sample operation is associated with optimizing a well planning operation.

The WPO application 1000 receives input data in response to an event-driven trigger and determines a target area and well parameters based on the input data (1102). The WPO application 1000 includes optimization methods that involve processing and analysis of 1D, 2D, and 3D geological models (1104). For example, the WPO application 1000 is based on probabilistic multi-dimensional modeling of reservoir quality with data describing risk estimations relating to the reservoir.

Based on the geological models, the WPO application 1000 is operable to generate one or more risk models (1106). For example, the WPO application 1000 is configured to model, in a 3D/multi-dimensional space, the risk of encountering poor quality reservoir rocks. In some implementations, the risk estimations are modeled in 3D by defining geological, geophysical, petrophysical, and reservoir engineering data constraints. One or more risk models of the WPO application 1000 are operable to generate one or more risk maps 1112 that are used to compute estimates of hydrocarbon reserves at particular areas of a reservoir in a given region. For example, the risk models can generate a porosity only risk map, a facies only risk map, and a porosity and facies risk map. In some implementations, WPO application 1000 includes risk models that are operable to generate a petrophysical & seismic AI risk map.

The WPO application 1000 is able to optimize well location data for a well plan based on risk models and using analytical rules related to the fast marching method (1108). For example, the WPO application 1000 determines new well trajectories using, for example, a 3D risk model to maximize reservoir contact and ensure optimal drainage of hydrocarbons. The WPO application 1000 allows for generating single or multiple well plan scenarios on the fly.

The WPO application 1000 is operable to generate an optimized well plan, including an event-driven trigger relating to the well plan (1110). The event-driven trigger can cause the WPO application to output an example optimized wells plan drilling plan 1114. The drilling plan 1114 may be output to at least the WAS module 314 for approval.

Figure 12:
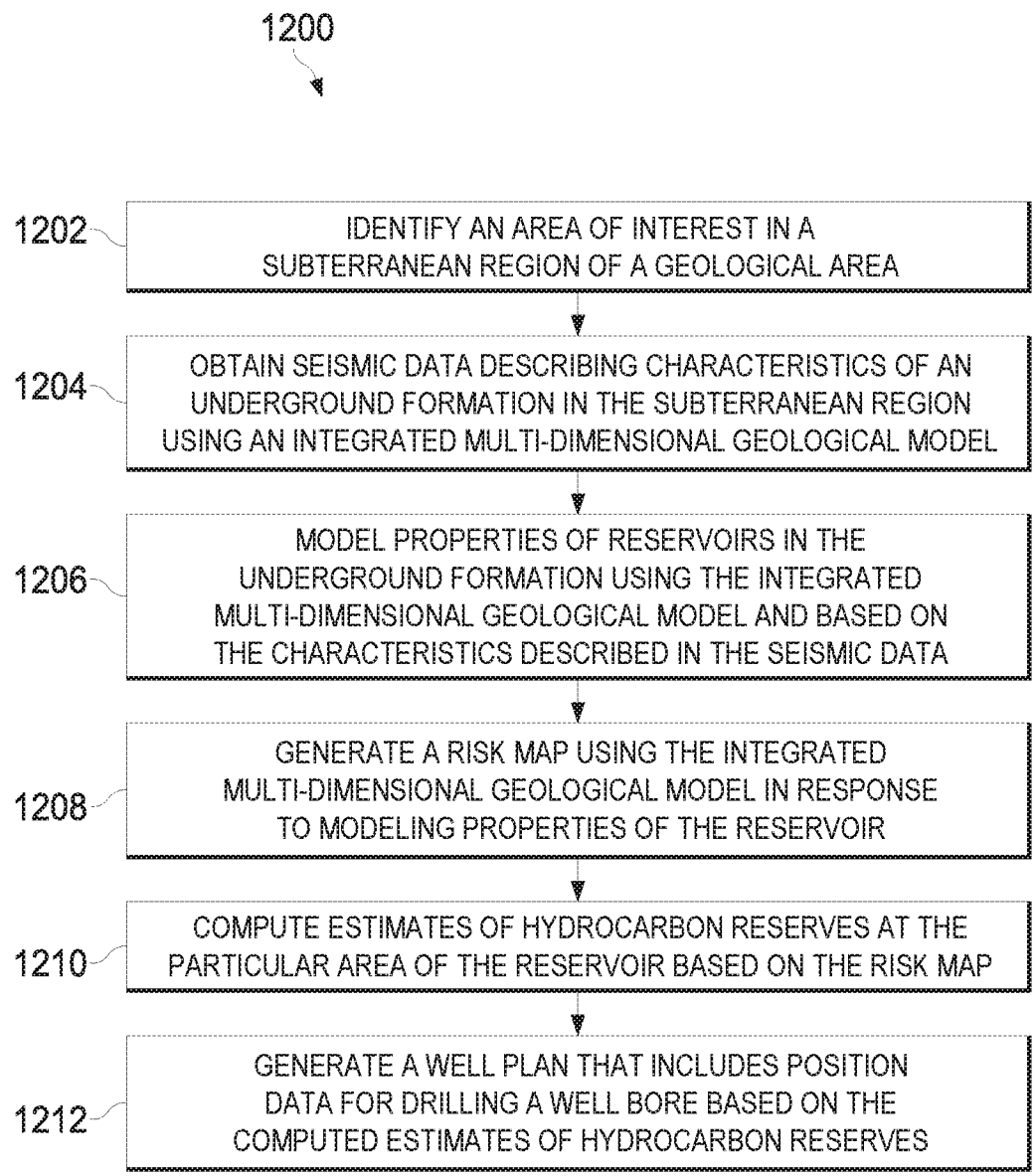
FIG. 12 is a flow diagram of an example process for generating a well plan for identifying hydrocarbon reserves of a subterranean region using a reservoir earth model.

FIG. 12 is a flow diagram of an example process 1200 for identifying hydrocarbon reserves of a subterranean region using a reservoir earth model. Similar to process 500 described above, process 1200 can also be implemented using the system 100. Hence, descriptions of process 1200 may reference the computing resources of system 100 described earlier in this document. In some implementations, the steps of process 1200 are enabled by programmed instructions executable by one or more processors of the devices and resources described in this document.

Referring now to process 1200, the system 100 is configured to identify an area of interest in a subterranean region of a geological area (1202). The system 100 can use the integrated multi-dimensional geological model to automatically identify and select geological formation tops/surfaces that correspond to the area of interest in the subterranean region. For example, the geological model is configured to identify geological formations based on data values of well logs or relevant seismic data obtained using sensor devices or geophones that transmit data communications to the computer systems 124.

The system 100 is configured to obtain seismic data describing characteristics of an underground formation in the subterranean region of the geological area (1204). For example, the system 100 uses the integrated multi-dimensional geological model to obtain seismic data that describes the density, porosity, and fluid content of the medium through which the seismic waves are traveling.

The system 100 models properties of reservoirs in the underground formation based on the characteristics described in the seismic data (1206). For example, the integrated multi-dimensional geological model of system 100 is configured to model based on data values in the seismic data that are descriptive of characteristics of the underground formation.

The system 100 generates a risk map that is used to estimate a probability of contacting a particular area of the reservoir (1208). For example, the system 100 is operable to use the integrated multi-dimensional geological model to generate the risk map in response to modeling properties of the reservoir. The risk map is configured to estimate probabilities that represent a predicted likelihood of contacting a particular area of the reservoir that has properties corresponding to at least one of the modeled properties.

The system 100 computes estimates of hydrocarbon reserves at the particular area of the reservoir (1210). For example, the integrated multi-dimensional geological model is configured to compute various types of estimates that are associated with the reservoir and the system 100 uses the geological model to compute estimates of hydrocarbon reserves at the particular area of the reservoir based at least on the risk map.

The system 100 generates a well plan using the integrated multi-dimensional geological model. For example, the system 100 generates the well plan based on the computed estimates of hydrocarbon reserves. The generated well plan includes position data for drilling a well bore to encounter the hydrocarbon reserves at the particular area of the reservoir (1212).

Figure 13:
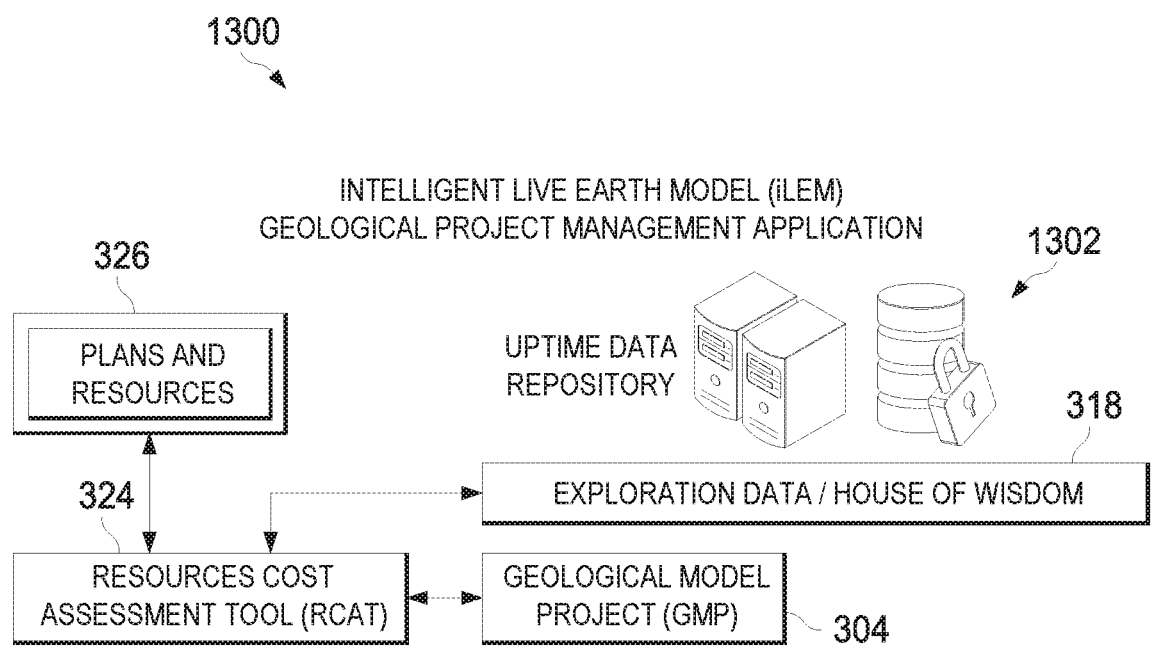
FIG. 13 is a block diagram of an example geological project management application.
Figure 14:
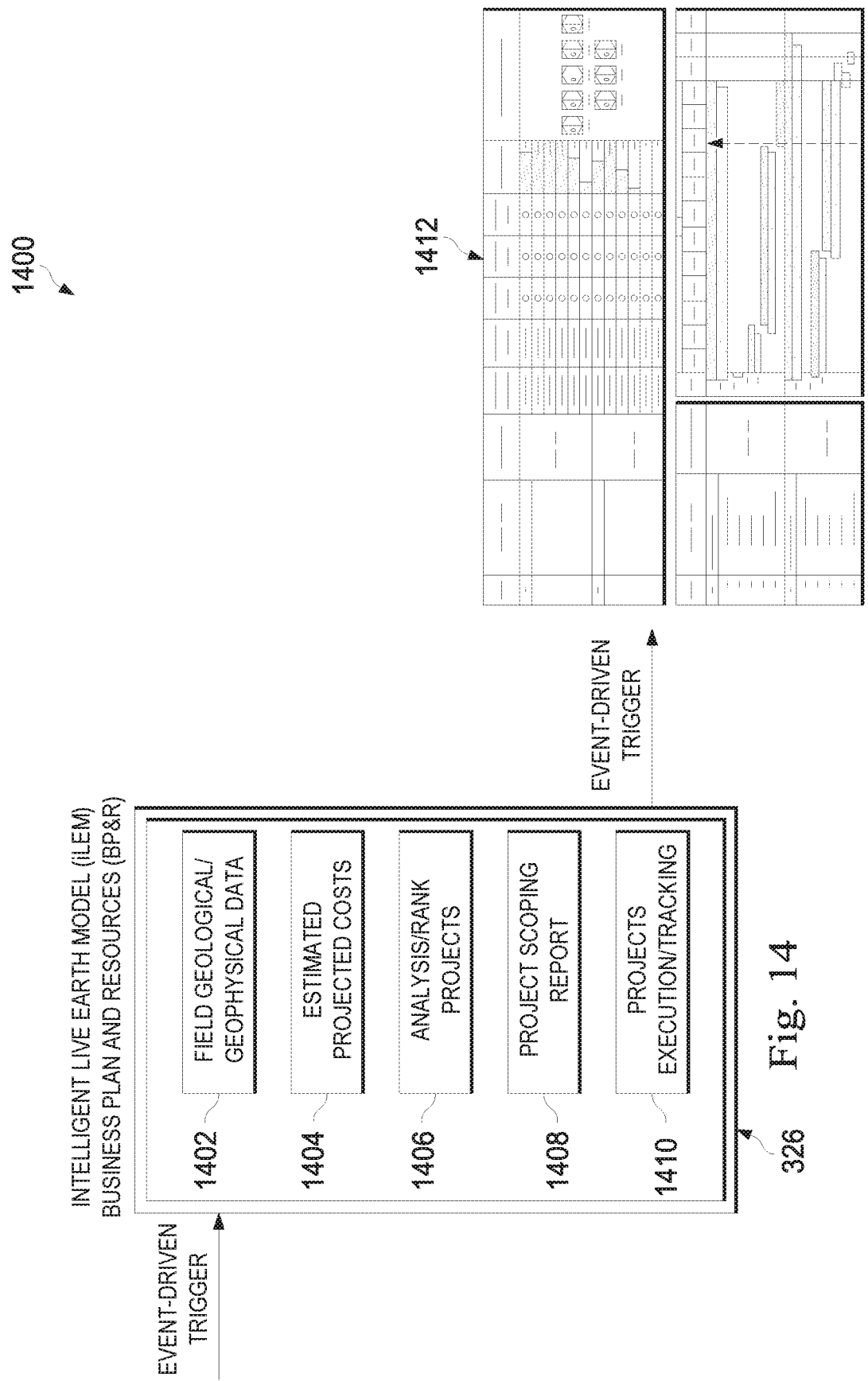
FIG. 14 is a block diagram that includes example steps of a business planning and resource allocation for a geological project.

FIG. 13 is a block diagram of an example geological project management application 1300. Relatedly, FIG. 14 is a block diagram that includes an example process 1400 that can be used to perform business planning and resource allocation for a geological project. In some cases, the geological project management application 1300 provides an autonomous workflow that receives new data from several resources and performs integrated 1D, 2D, and 3D geological modeling. In other cases, geological project management application 1300 provides a specialized process to enhance business performance within an organization that is tasked with efficient performance of hydrocarbon exploration. In some instances, the geological project management application 1300 includes functionality relating to the GMP module 304 and the plans & resources module 326, each of which were described earlier with reference to FIG. 3.

A sample operation will be described to illustrate the business planning and resource allocation process 1400 of the geological project management application with reference to the embodiment of FIG. 13. In the example of FIG. 1300 the sample operation is determining an allocation of resources required to execute a geological project.

The geological project management application 1300 receives input data corresponding to field geological/geophysical data for one or more project in response to an event-driven trigger (1402). For example, the geological project management application 1300 can receive field business plan requirements including available budgets, information describing personnel/human resources, seismic acquisition devices and sensors, and drilling rigs.

The geological project management application 1300 determines an estimated projected cost or estimated cost projection for each of the one or more projects (1404). For example, each of the exploration data module 318 and the GMP module 304 can provide information describing geological database components such as number of formation tops, quantity of reservoir zones, core plugs, the number of hydrocarbon tests, and datasets for seismic traces. The geological project management application 1300 is operable to determine the estimated cost projections for the projects based on the information describing the geological database components.

The geological project management application 1300 analyzes data pertaining to each of the projects and proceeds to rank each project (1406). For example, the geological project management application 1300 analyzes data pertaining to estimated man-months for a geoscience task. In some implementations, the geological project management application 1300 analyzes the data against known quantities, such as by comparing estimated costs of discrete geoscience tasks with known/actual costs. In some examples, the geological project management application 1300 may also include a component for determining and comparing cost estimates for different reservoir complexity levels.

The geological project management application 1300 generates one or more project scoping reports in accordance with analysis of the data pertaining to each of the projects (1408). For example, the geological project management application 1300 is operable to generate scoping reports that correspond to enhanced business and field performances reports. The scoping/field performance reports can include structured plans and techniques for minimizing costs and enhancing revenues in the form of available resources to be converted to hydrocarbon reserves.

The geological project management application 1300 allocates resources for project execution and tracking of project tasks and deliverables (1410). The geological project management application 1300 can also predict and model the impact of changes to the example geoscience tasks on the cost of a project as a whole. In some implementations, the geological project management application 1300 is part of a business planning and resource management system that provides a comprehensive and innovative tool for accomplishing hydrocarbon exploration and subsurface characterization of a targeted reservoir.

The resource management system can generate example graphical data 1412 that encompasses all aspects of exploration and reservoir characterization projects from a scoping stage to a final output stage where a project deliverable is generated. The geological project management application 1300 is operable to provide a holistic view for stakeholders, including business plans, cost assessment, project managers, and resource managers for improved manpower and resource allocations.

Moreover, each of the geological project management application 1300 and resource management system are able to capture project statistics and assets in a secure and classified manner within an example data repository of the REM. The stored information can be appropriately indexed to facilitate future data mining and analytics. The benefits of having such a tool include enhanced project scoping, efficient execution of multiple projects at a lower cost relative top prior approaches, accurate estimation of project timelines and deliverables, sophisticated reporting at frequent intervals, and reductions in administrative overhead.

FIG. 15 illustrates a table 1500 that shows examples of estimated time savings for modules of an example reservoir earth model. In general, an REM represented by an integrated multi-dimensional geological model not only does automation to help professionals and management save time, but the integrated models also assist in collecting and analyzing geoscience data much faster than existing methods. As the integrated models iteratively enhance the data quality generated at the system, the system is also able to improve upon its analytical framework for generating predictions and increasing the speed in which it generates accurate responses to complex queries.

Figure 16:
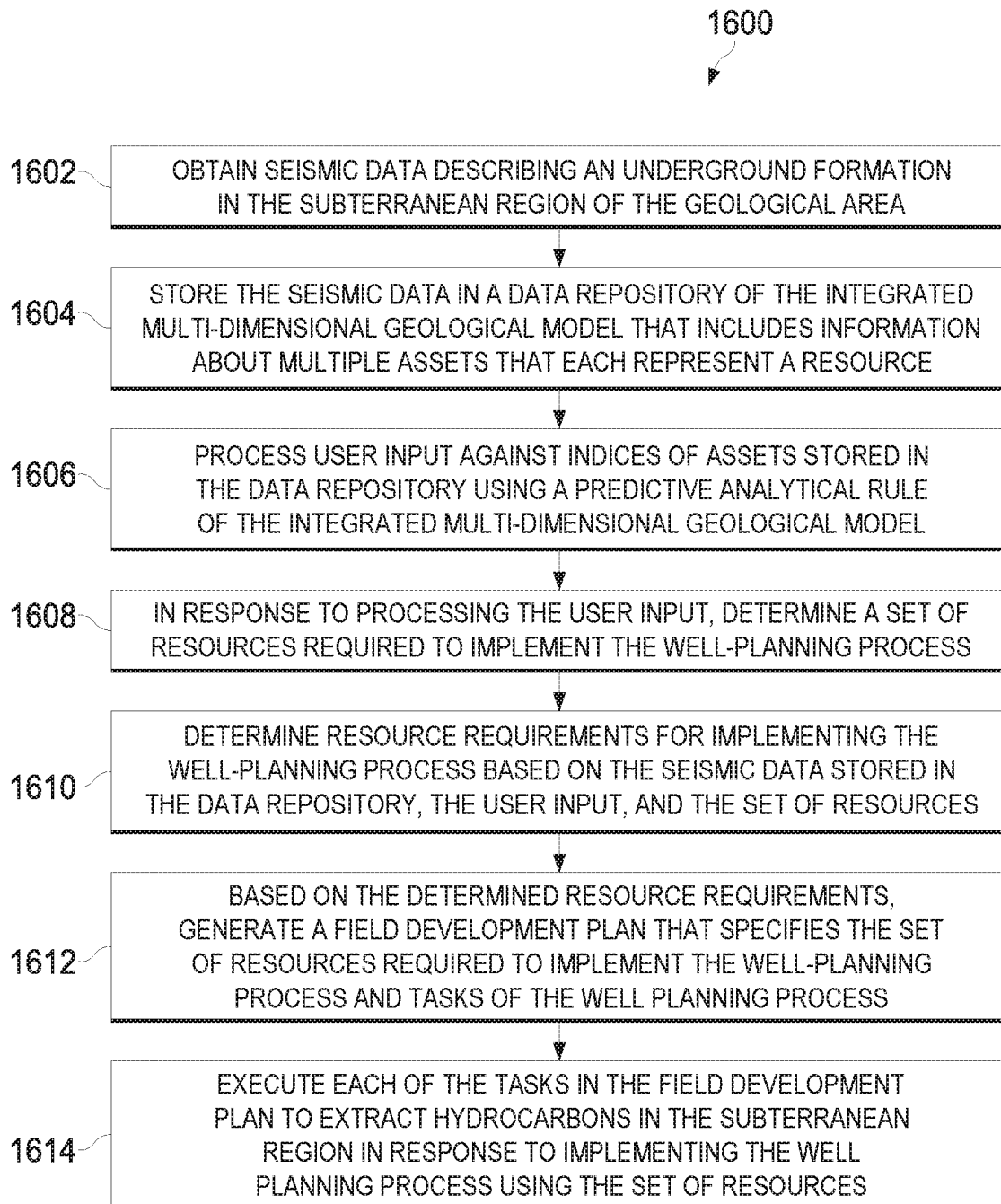
FIG. 16 is a flow diagram of an example process for allocating resources used to implement a well-planning operation.

FIG. 16 is a flow diagram of an example process 1600 for allocating resources used to implement a well-planning operation. Similar to processes 500 and 1200 described earlier, process 1600 can also be implemented using the system 100. Hence, descriptions of process 1600 may reference the computing resources of system 100 described earlier in this document. In some implementations, the steps of process 1600 are enabled by programmed instructions executable by one or more processors of the devices and resources described in this document.

Referring now to process 1600, an integrated multi-dimensional geological model of system 100 obtains seismic data describing an underground formation in the subterranean region of the geological area (1602). The obtained seismic data is stored in a data repository of the integrated multi-dimensional geological model, where the data repository includes information about multiple assets and each asset of the multiple assets represents a resource (1604).

The system 100 determines resource requirements for implementing the well-planning process based on the information that includes the seismic data stored in the data repository (1610). Determining the resource requirements includes processing user input against indices of assets stored in the data repository using a predictive analytical rule of the integrated multi-dimensional geological model (1606). Determining the resource requirements further includes, in response to processing the user input, determining a set of resources required to implement the well-planning process based on: i) a control variable of the user input corresponding to a task of the well planning process and ii) geological properties of reservoirs in the underground formation indicated by the obtained seismic data (1608).

The integrated multi-dimensional geological model generates a field development plan based on the determined resource requirements and the user input. The field development plan specifies the set of resources required to implement the well-planning process and one or more tasks of the well planning process (1612). The system 100 executes each of the one or more tasks in the field development plan using the set of resources (1614). For example, the system 100 is operable to execute each of the tasks in the field development plan to extract hydrocarbons in the subterranean region in response to implementing the well planning process using at least one resource in the set of resources.

Figure 17:
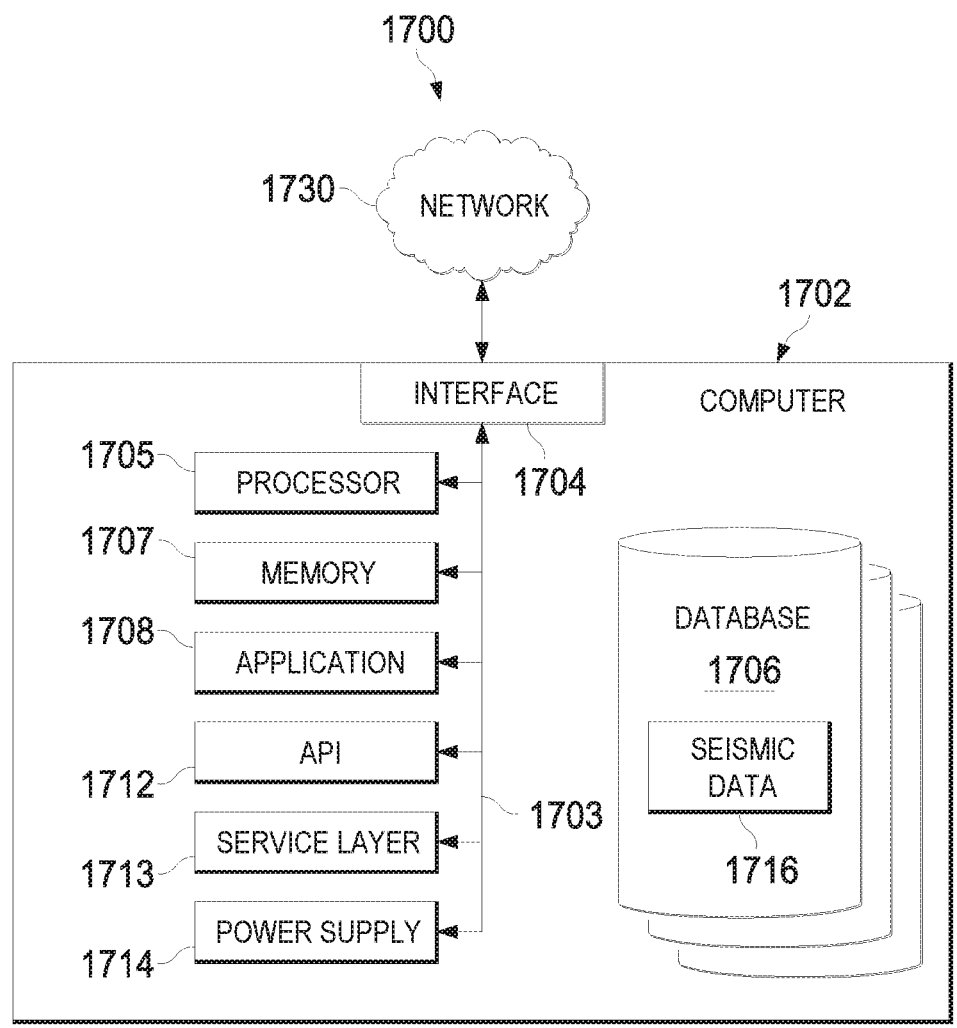
FIG. 17 is a block diagram illustrating an example computer system used to provide computational functionalities associated with described algorithms, methods, functions, processes, flows, and procedures according to some implementations of the present disclosure.

FIG. 17 is a block diagram of an example computer system 1700 used to provide computational functionalities associated with described algorithms, methods, functions, processes, flows, and procedures described in the present disclosure, according to some implementations of the present disclosure.

The illustrated computer 1702 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 1702 can include input devices such as keypads, keyboards, and touch screens that can accept user information. Also, the computer 1702 can include output devices that can convey information associated with the operation of the computer 1702. The information can include digital data, visual data, audio information, or a combination of information. The information can be presented in a graphical user interface (UI) (or GUI).

The computer 1702 can serve in a role as a client, a network component, a server, a database, a persistency, or components of a computer system for performing the subject matter described in the present disclosure. The illustrated computer 1702 is communicably coupled with a network 1730. In some implementations, one or more components of the computer 1702 can be configured to operate within different environments, including cloud-computing-based environments, local environments, global environments, and combinations of environments.

Generally, the computer 1702 is an electronic computing device operable to receive, transmit, process, store, and manage data and information associated with the described subject matter. According to some implementations, the computer 1702 can also include, or be communicably coupled with, an application server, an email server, a web server, a caching server, a streaming data server, or a combination of servers.

The computer 1702 can receive requests over network 1730 from a client application (for example, executing on another computer 1702). The computer 1702 can respond to the received requests by processing the received requests using software applications. Requests can also be sent to the computer 1702 from internal users (for example, from a command console), external (or third) parties, automated applications, entities, individuals, systems, and computers.

Each of the components of the computer 1702 can communicate using a system bus 1703. In some implementations, any or all of the components of the computer 1702, including hardware or software components, can interface with each other or the interface 1704 (or a combination of both), over the system bus 1703. Interfaces can use an application programming interface (API) 1712, a service layer 1713, or a combination of the API 1712 and service layer 1713. The API 1712 can include specifications for routines, data structures, and object classes. The API 1712 can be either computer-language independent or dependent. The API 1712 can refer to a complete interface, a single function, or a set of APIs.

The service layer 1713 can provide software services to the computer 1702 and other components (whether illustrated or not) that are communicably coupled to the computer 1702. The functionality of the computer 1702 can be accessible for all service consumers using this service layer. Software services, such as those provided by the service layer 1713, can provide reusable, defined functionalities through a defined interface. For example, the interface can be software written in JAVA, C++, or a language providing data in extensible markup language (XML) format. While illustrated as an integrated component of the computer 1702, in alternative implementations, the API 1712 or the service layer 1713 can be stand-alone components in relation to other components of the computer 1702 and other components communicably coupled to the computer 1702. Moreover, any or all parts of the API 1712 or the service layer 1713 can be implemented as child or sub-modules of another software module, enterprise application, or hardware module without departing from the scope of the present disclosure.

The computer 1702 includes an interface 1704. Although illustrated as a single interface 1704 in FIG. 17, two or more interfaces 1704 can be used according to particular needs, desires, or particular implementations of the computer 1702 and the described functionality. The interface 1704 can be used by the computer 1702 for communicating with other systems that are connected to the network 1730 (whether illustrated or not) in a distributed environment. Generally, the interface 1704 can include, or be implemented using, logic encoded in software or hardware (or a combination of software and hardware) operable to communicate with the network 1730. More specifically, the interface 1704 can include software supporting one or more communication protocols associated with communications. As such, the network 1730 or the interface's hardware can be operable to communicate physical signals within and outside of the illustrated computer 1702.

The computer 1702 includes a processor 1705. Although illustrated as a single processor 1705 in FIG. 17, two or more processors 1705 can be used according to particular needs, desires, or particular implementations of the computer 1702 and the described functionality. Generally, the processor 1705 can execute instructions and can manipulate data to perform the operations of the computer 1702, including operations using algorithms, methods, functions, processes, flows, and procedures as described in the present disclosure.

The computer 1702 also includes a database 1706 that can hold data, including seismic data 1716 (for example, seismic data described earlier at least with reference to FIG. 1), for the computer 1702 and other components connected to the network 1730 (whether illustrated or not). For example, database 1706 can be an in-memory, conventional, or a database storing data consistent with the present disclosure. In some implementations, database 1706 can be a combination of two or more different database types (for example, hybrid in-memory and conventional databases) according to particular needs, desires, or particular implementations of the computer 1702 and the described functionality. Although illustrated as a single database 1706 in FIG. 17, two or more databases (of the same, different, or combination of types) can be used according to particular needs, desires, or particular implementations of the computer 1702 and the described functionality. While database 1706 is illustrated as an internal component of the computer 1702, in alternative implementations, database 1706 can be external to the computer 1702.

The computer 1702 also includes a memory 1707 that can hold data for the computer 1702 or a combination of components connected to the network 1730 (whether illustrated or not). Memory 1707 can store any data consistent with the present disclosure. In some implementations, memory 1707 can be a combination of two or more different types of memory (for example, a combination of semiconductor and magnetic storage) according to particular needs, desires, or particular implementations of the computer 1702 and the described functionality. Although illustrated as a single memory 1707 in FIG. 17, two or more memories 1707 (of the same, different, or combination of types) can be used according to particular needs, desires, or particular implementations of the computer 1702 and the described functionality. While memory 1707 is illustrated as an internal component of the computer 1702, in alternative implementations, memory 1707 can be external to the computer 1702.

The application 1708 can be an algorithmic software engine providing functionality according to particular needs, desires, or particular implementations of the computer 1702 and the described functionality. For example, application 1708 can serve as one or more components, modules, or applications. Further, although illustrated as a single application 1708, the application 1708 can be implemented as multiple applications 1708 on the computer 1702. In addition, although illustrated as internal to the computer 1702, in alternative implementations, the application 1708 can be external to the computer 1702.

The computer 1702 can also include a power supply 1714. The power supply 1714 can include a rechargeable or non-rechargeable battery that can be configured to be either user- or non-user-replaceable. In some implementations, the power supply 1714 can include power-conversion and management circuits, including recharging, standby, and power management functionalities. In some implementations, the power-supply 1714 can include a power plug to allow the computer 1702 to be plugged into a wall socket or a power source to, for example, power the computer 1702 or recharge a rechargeable battery.

There can be any number of computers 1702 associated with, or external to, a computer system containing computer 1702, with each computer 1702 communicating over network 1730. Further, the terms "client," "user," and other appropriate terminology can be used interchangeably, as appropriate, without departing from the scope of the present disclosure. Moreover, the present disclosure contemplates that many users can use one computer 1702 and one user can use multiple computers 1702.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/-R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship. Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

Particular embodiments of the subject matter have been described. Other embodiments are within the scope of the following claims. For example, the actions recited in the claims can be performed in a different order and still achieve desirable results. As one example, some processes depicted in the accompanying figures do not necessarily require the particular order shown, or sequential order, to achieve desirable results.

What is claimed is:

1. A computer-implemented method for determining characteristics of an underground formation in a subterranean region of a geological area, the method comprising:
   obtaining a first wavefield represented by seismic data generated from a plurality of sampling sensors, wherein a subset of the sampling sensors are deployed in the subterranean region;
   providing data values of the seismic data that indicate properties of the underground formation as inputs to a machine-learning engine configured to generate one or more models;
   processing the inputs corresponding to data values of the seismic data using the machine-learning engine;
   in response to processing the data values of the seismic data, generating a plurality of predictive models, each predictive model comprising a neural network having interconnected nodes that are configured to determine geological properties of a layer in the underground formation based on a respective analytical rule of the predictive model;
   providing, to each of the predictive models, new data values of seismic data representing a second wavefield obtained using the subset of sampling sensors;
   automatically updating the respective analytical rule of each predictive model in response to processing the new data values of seismic data at the predictive model; and
   determining, from the new data values of seismic data, (i) a first geological property of the layer using the updated analytical rule of a first predictive model and (ii) a second, different geological property of the layer using the updated analytical rule of a second, different predictive model.

2. The method of claim 1, comprising:
   generating an integrated multi-dimensional geological model based on the plurality of predictive models, wherein the integrated multi-dimensional geological model is configured to model characteristics of reservoirs in the subterranean region to estimate hydrocarbon reserves using at least the first and second geological properties of the layer in the underground formation.

3. The method of claim 2, wherein obtaining each of the first and second wavefields comprises:
   obtaining each of the first and second wavefields in response to drilling the subterranean region to penetrate one or more layers in the underground formation.

4. The method of claim 3, comprising:
   determining, by the integrated multi-dimensional geological model, a position of one or more well bores in the subterranean region based on the modeled characteristics of reservoirs in the subterranean region and estimates of hydrocarbon reserves in the reservoirs.

5. The method of claim 3, comprising:
   determining respective quality measures of sediments in each of the one or more layers using each predictive model of the plurality of predictive models; and
   based on the respective quality measure of sediments in each of the one or more layers, determining, by the integrated multi-dimensional geological model, a trajectory for drilling the subterranean region to penetrate the one or more layers in the underground formation.

6. The method of claim 1, wherein generating the plurality of predictive models comprises:
   generating a three-dimensional geological numerical model configured to predict numerical values indicating one or more properties of the layer in the underground formation.

7. The method of claim 6, wherein generating the plurality of predictive models comprises generating a plurality of permanently active autonomous predictive models.

8. The method of claim 1, wherein processing the inputs corresponding to the data values of the seismic data comprises:
   processing the inputs using one or more neural networks of the machine-learning engine based on analytical rules executed at the machine-learning engine, wherein each of the one or more neural network is configured to represent a respective data model of the machine-learning engine.

9. The method of claim 8, wherein:
   at least one of the analytical rules is a deep-learning algorithm that is executed to process the inputs through one or more layers of a neural network; and the neural network is implemented on a hardware circuit accessible by the machine-learning engine.

10. The method of claim 1,
wherein at least one predictive model is configured to determine formation tops of the layer and at least one predictive model is configured to determine a geological property of the layer other than the top of the layer;
the method further comprising generating an integrated multi-dimensional geological model based on the plurality of predictive models, wherein the integrated multi-dimensional geological model is configured to determine suitable locations for deviated wells in the formation.

11. A system for determining characteristics of an underground formation in a subterranean region of a geological area, the system comprising:
one or more processing devices and one or more non-transitory machine-readable storage devices storing instructions that are executable by the one or more processing devices to cause performance of operations comprising:
obtaining a first wavefield represented by seismic data generated from a plurality of sampling sensors, wherein a subset of the sampling sensors are deployed in the subterranean region;
providing data values of the seismic data that indicate properties of the underground formation as inputs to a machine-learning engine configured to generate one or more models;
processing the inputs corresponding to data values of the seismic data using the machine-learning engine;
in response to processing the data values of the seismic data, generating a plurality of predictive models, each predictive model comprising a neural network having interconnected nodes that are configured to determine geological properties of a layer in the underground formation based on a respective analytical rule of the predictive model;
providing, to each of the predictive models, new data values of seismic data representing a second wavefield obtained using the subset of sampling sensors;
automatically updating the respective analytical rule of each predictive model in response to processing the new data values of seismic data at the predictive model; and
determining, from the new data values of seismic data, (i) a first geological property of the layer using the updated analytical rule of a first predictive model and (ii) a second, different geological property of the layer using the updated analytical rule of a second, different predictive model.

12. The system of claim 11, wherein the operations comprise:
generating an integrated multi-dimensional geological model based on the plurality of predictive models, wherein the integrated multi-dimensional geological model is configured to model characteristics of reservoirs in the subterranean region to estimate hydrocarbon reserves using at least the first and second geological properties of the layer in the underground formation.

13. The system of claim 12, wherein obtaining each of the first and second wavefields comprises:
obtaining each of the first and second wavefields in response to drilling the subterranean region to penetrate one or more layers in the underground formation.

14. The system of claim 13, wherein the operations comprise:
determining, by the integrated multi-dimensional geological model, a position of one or more well bores in the subterranean region based on the modeled characteristics of reservoirs in the subterranean region and estimates of hydrocarbon reserves in the reservoirs.

15. The system of claim 13, wherein the operations comprise:
determining respective quality measures of sediments in each of the one or more layers using each predictive model of the plurality of predictive models; and
based on the respective quality measure of sediments in each of the one or more layers, determining, by the integrated multi-dimensional geological model, a trajectory for drilling the subterranean region to penetrate the one or more layers in the underground formation.

16. The system of claim 11, wherein generating the plurality of predictive models comprises:
generating a three-dimensional geological numerical model configured to predict numerical values indicating one or more properties of the layer in the underground formation.

17. The system of claim 16, wherein generating the plurality of predictive models comprises generating a plurality of permanently active autonomous predictive models.

18. The system of claim 11, wherein processing the inputs corresponding to the data values of the seismic data comprises:
processing the inputs using one or more neural networks of the machine-learning engine based on analytical rules executed at the machine-learning engine, wherein each of the one or more neural network is configured to represent a respective data model of the machine-learning engine.

19. The system of claim 18, wherein:
at least one of the analytical rules is a deep-learning algorithm that is executed to process the inputs through one or more layers of a neural network; and
the neural network is implemented on a hardware circuit accessible by the machine-learning engine.

20. The system of claim 11, wherein at least one predictive model is configured to determine formation tops of the layer and at least one predictive model is configured to determine a geological property of the layer other than the top of the layer, the operations further comprising:
generating an integrated multi-dimensional geological model based on the plurality of predictive models, wherein the integrated multi-dimensional geological model is configured to determine suitable locations for deviated wells in the formation.

* * * * *